United States Patent
Hilscher et al.

(10) Patent No.: US 7,979,939 B2
(45) Date of Patent: Jul. 19, 2011

(54) DENTAL CLEANING DEVICE

(75) Inventors: Alexander Hilscher, Kronberg (DE); Hansjorg Reick, Steinbach (DE); Armin Schwarz-Hartmann, Wendelsheim (DE); Peter Trawinski, Weiterstadt (DE); Martin Stratmann, Frankfurt (DE); Wolfgang Vorbeck, Idstein-Eschenhahn (DE)

(73) Assignee: Braun GmbH, Krongberg (DE)

( * ) Notice: Subject to any disclaimer, the term of this patent is extended or adjusted under 35 U.S.C. 154(b) by 0 days.

(21) Appl. No.: 12/627,367

(22) Filed: Nov. 30, 2009

(65) Prior Publication Data

US 2010/0162500 A1 Jul. 1, 2010

Related U.S. Application Data

(63) Continuation of application No. 10/871,469, filed on Jun. 18, 2004, now Pat. No. 7,624,467, which is a continuation of application No. 09/811,080, filed on Mar. 16, 2001, now Pat. No. 7,086,111.

(51) Int. Cl.
*A61C 17/22* (2006.01)
*A46B 13/02* (2006.01)

(52) U.S. Cl. ............................................ 15/22.1; 15/28

(58) Field of Classification Search ................. 15/22.1, 15/22.2, 23, 28
See application file for complete search history.

(56) References Cited

U.S. PATENT DOCUMENTS

| | | | |
|---|---|---|---|
| 2,798,241 A | 7/1957 | Cohen | |
| 3,109,619 A | 11/1963 | Krug et al. | |
| 3,220,039 A | 11/1965 | Dayton et al. | |
| 3,417,417 A | 12/1968 | Rhodes | |
| 3,461,874 A | 8/1969 | Martinez | |
| 3,496,500 A | 2/1970 | Romary | |
| 3,571,544 A | 3/1971 | Sheehan | |
| 3,782,799 A | 1/1974 | Hansen | |
| 3,796,850 A | 3/1974 | Moreland, II et al. | |
| 3,802,420 A | 4/1974 | Moffat et al. | |
| 3,810,147 A | 5/1974 | Lichtblau | |
| 3,904,841 A | 9/1975 | Swatman | |
| 4,156,620 A | 5/1979 | Clemens | |
| 4,274,070 A | 6/1981 | Thiene | |
| 4,333,197 A | 6/1982 | Kuris | |
| 4,349,814 A | 9/1982 | Akehurst | |
| 4,352,098 A | 9/1982 | Stephen et al. | |
| 4,365,376 A | 12/1982 | Oda et al. | |

(Continued)

FOREIGN PATENT DOCUMENTS

CN 2048697 12/1989

(Continued)

OTHER PUBLICATIONS

Use instructions to Braun D5 electric toothbrush Type 4726 on sale in United States, circa 1991 (3 sheets—cover and pp. 8-11) including description of "Travel lock" switch.

(Continued)

*Primary Examiner* — Randall Chin
(74) *Attorney, Agent, or Firm* — John P. Colbert

(57) ABSTRACT

The invention is directed to a dental cleaning device. It relates in particular to a handle section of an electric toothbrushing device, with a coupling section for coupling various cleaning tools thereto, a drive mechanism for driving the coupled cleaning tool, and a control device for controlling the drive mechanism. The invention further relates to such cleaning tools. According to the invention the handle section includes an electronic interlock device which is deactivated by an encoded interlock canceling element on the cleaning tool only when the cleaning tool is coupled to the handle section.

1 Claim, 24 Drawing Sheets

U.S. PATENT DOCUMENTS

| | | | |
|---|---|---|---|
| 4,371,118 | A | 2/1983 | Sontheimer et al. |
| 4,413,199 | A | 11/1983 | Fischer |
| 4,492,574 | A | 1/1985 | Warrin et al. |
| 4,502,497 | A | 3/1985 | Siahou |
| 4,506,400 | A | 3/1985 | Klein |
| 4,514,172 | A | 4/1985 | Behringer |
| 4,523,083 | A | 6/1985 | Hamilton |
| 4,546,266 | A | 10/1985 | Zenick et al. |
| 4,595,850 | A | 6/1986 | Woog |
| 4,682,584 | A | 7/1987 | Pose |
| 4,698,869 | A | 10/1987 | Mierau et al. |
| 4,704,602 | A | 11/1987 | Asbrink |
| 4,716,614 | A | 1/1988 | Jones et al. |
| 4,736,207 | A | 4/1988 | Siikaria et al. |
| 4,820,152 | A | 4/1989 | Warrin et al. |
| 4,827,550 | A | 5/1989 | Graham et al. |
| 4,845,796 | A | 7/1989 | Mosley |
| 4,878,679 | A | 11/1989 | Plank et al. |
| 4,900,252 | A | 2/1990 | Liefke et al. |
| 4,910,634 | A | 3/1990 | Pipkorn |
| 4,914,376 | A | 4/1990 | Meyer |
| 5,014,794 | A | 5/1991 | Hansson |
| 5,065,137 | A | 11/1991 | Herman |
| 5,072,164 | A | 12/1991 | Pruis et al. |
| 5,099,536 | A | 3/1992 | Hirabayashi |
| 5,165,131 | A | 11/1992 | Staar |
| 5,184,959 | A | 2/1993 | Oryhon et al. |
| 5,189,751 | A | 3/1993 | Giuliani |
| 5,217,478 | A | 6/1993 | Rexroth |
| 5,233,323 | A | 8/1993 | Burkett et al. |
| 5,263,218 | A | 11/1993 | Giuliani et al. |
| 5,269,794 | A | 12/1993 | Rexroth |
| 5,289,604 | A | 3/1994 | Kressner |
| 5,305,492 | A | 4/1994 | Giuliani et al. |
| 5,337,435 | A | 8/1994 | Krasner et al. |
| 5,341,534 | A | 8/1994 | Serbinski et al. |
| 5,355,544 | A | 10/1994 | Dirksing |
| 5,378,153 | A | 1/1995 | Giuliani et al. |
| 5,381,576 | A | 1/1995 | Hwang |
| 5,392,028 | A | 2/1995 | Pichl |
| 5,502,861 | A | 4/1996 | Spieler et al. |
| 5,544,382 | A | 8/1996 | Giuliani et al. |
| 5,561,881 | A | 10/1996 | Klinger et al. |
| 5,576,693 | A | 11/1996 | Tyren et al. |
| 5,577,285 | A | 11/1996 | Drossler |
| 5,673,451 | A | 10/1997 | Moore et al. |
| 5,693,042 | A | 12/1997 | Boiarski et al. |
| 5,749,885 | A | 5/1998 | Sjostrom et al. |
| 5,760,580 | A | 6/1998 | Tyren |
| 5,781,955 | A | 7/1998 | Hendricks |
| 5,784,742 | A | 7/1998 | Giuliani et al. |
| 5,812,065 | A | 9/1998 | Schrott et al. |
| 5,864,288 | A | 1/1999 | Hogan |
| 5,888,031 | A | 3/1999 | Buck et al. |
| 5,897,315 | A | 4/1999 | Nakayama et al. |
| 5,939,983 | A | 8/1999 | Rudell et al. |
| 5,943,723 | A | 8/1999 | Hilfinger et al. |
| 5,974,615 | A | 11/1999 | Schwarz-Hartmann |
| 5,998,965 | A | 12/1999 | Carlucci et al. |
| 6,017,354 | A | 1/2000 | Culp et al. |
| 6,029,303 | A | 2/2000 | Dewan |
| 6,043,646 | A | 3/2000 | Jansseune |
| 6,140,723 | A | 10/2000 | Matsui et al. |
| 6,163,258 | A | 12/2000 | Rudell et al. |
| 6,177,870 | B1 | 1/2001 | Lian et al. |
| 6,193,510 | B1 | 2/2001 | Tsimerman |
| 6,195,828 | B1 | 3/2001 | Fritsch |
| 6,202,242 | B1 | 3/2001 | Salmon et al. |
| 6,212,052 | B1 | 4/2001 | Heuer et al. |
| 6,227,853 | B1 | 5/2001 | Hansen et al. |
| 6,234,051 | B1 | 5/2001 | Bareggi |
| 6,265,789 | B1 | 7/2001 | Honda et al. |
| 6,326,884 | B1 | 12/2001 | Wohlrabe |
| 6,359,559 | B1 | 3/2002 | Rudell et al. |
| 6,367,108 | B1 | 4/2002 | Fritsch et al. |
| 6,389,633 | B1 | 5/2002 | Rosen |
| 6,422,566 | B1 | 7/2002 | Rudell et al. |
| 6,453,497 | B1 | 9/2002 | Chiang et al. |
| 6,531,873 | B1 | 3/2003 | Wohlrabe |
| 6,536,068 | B1 | 3/2003 | Yang et al. |
| 6,545,576 | B1 | 4/2003 | Marchini et al. |
| 6,590,763 | B2 | 7/2003 | Kishimoto |
| 6,611,780 | B2 | 8/2003 | Lundell et al. |
| 6,623,698 | B2 | 9/2003 | Kuo |
| 6,636,135 | B1 | 10/2003 | Vetter |
| 6,648,641 | B1 | 11/2003 | Viltro et al. |
| 6,731,213 | B1 | 5/2004 | Smith |
| 6,734,795 | B2 | 5/2004 | Price |
| 6,735,802 | B1 | 5/2004 | Lundell et al. |
| 6,750,747 | B2 | 6/2004 | Mandell et al. |
| 6,754,928 | B1 | 6/2004 | Rosen |
| 6,792,640 | B2 | 9/2004 | Lev |
| 6,850,167 | B2 | 2/2005 | Rosen |
| 6,868,919 | B1 | 3/2005 | Manschitz et al. |
| 6,952,855 | B2 | 10/2005 | Lev et al. |
| 6,954,961 | B2 | 10/2005 | Ferber et al. |
| 7,024,717 | B2 | 4/2006 | Hilscher et al. |
| 7,067,945 | B2 | 6/2006 | Grez et al. |
| 7,086,111 | B2 | 8/2006 | Hilscher et al. |
| 7,174,972 | B2 | 2/2007 | Kristen et al. |
| 7,207,080 | B2 | 4/2007 | Hilscher et al. |
| 7,248,892 | B2 | 7/2007 | White et al. |
| 7,258,546 | B2 | 8/2007 | Beier et al. |
| 7,313,422 | B2 | 12/2007 | White et al. |
| 7,373,170 | B2 | 5/2008 | White et al. |
| 7,376,439 | B2 | 5/2008 | White et al. |
| 2002/0088068 | A1 | 7/2002 | Levy et al. |
| 2002/0129454 | A1 | 9/2002 | Hilscher et al. |
| 2002/0133308 | A1 | 9/2002 | Lundell et al. |
| 2002/0196113 | A1 | 12/2002 | Rudd et al. |
| 2003/0017874 | A1 | 1/2003 | Jianfei et al. |
| 2003/0085687 | A1 | 5/2003 | Stratmann et al. |
| 2003/0093103 | A1 | 5/2003 | Malackowski et al. |
| 2003/0101526 | A1 | 6/2003 | Hilscher |
| 2003/0115694 | A1 | 6/2003 | Pace |
| 2003/0131427 | A1 | 7/2003 | Hilscher et al. |
| 2003/0165794 | A1 | 9/2003 | Matoba |
| 2004/0220602 | A1 | 11/2004 | Deng et al. |
| 2004/0255409 | A1 | 12/2004 | Hilscher et al. |
| 2004/0267297 | A1 | 12/2004 | Malackowski |
| 2005/0000044 | A1 | 1/2005 | Hilscher et al. |
| 2005/0011025 | A1 | 1/2005 | Hilscher et al. |
| 2005/0050658 | A1 | 3/2005 | Chan et al. |
| 2005/0100867 | A1 | 5/2005 | Hilscher et al. |
| 2005/0128051 | A1 | 6/2005 | Dickinson et al. |
| 2005/0269403 | A1 | 12/2005 | White et al. |
| 2005/0271531 | A1 | 12/2005 | Brown, Jr. et al. |
| 2005/0272001 | A1 | 12/2005 | Blain et al. |
| 2005/0272002 | A1 | 12/2005 | Chenvainu et al. |
| 2006/0048797 | A1 | 3/2006 | Jung et al. |
| 2006/0066448 | A1 | 3/2006 | Berisford et al. |
| 2006/0074405 | A1 | 4/2006 | Malackowski et al. |
| 2006/0096046 | A1 | 5/2006 | Hilscher et al. |
| 2006/0145871 | A1 | 7/2006 | Donati et al. |
| 2006/0159533 | A1 | 7/2006 | Zeiler et al. |
| 2007/0001005 | A1 | 1/2007 | White et al. |
| 2007/0234493 | A1 | 10/2007 | Hilscher et al. |
| 2008/0010771 | A1 | 1/2008 | Hilscher et al. |
| 2008/0020351 | A1 | 1/2008 | Hilscher et al. |
| 2008/0020352 | A1 | 1/2008 | Hilscher et al. |
| 2008/0022469 | A1 | 1/2008 | Hilscher et al. |
| 2008/0022470 | A1 | 1/2008 | Hilscher et al. |
| 2008/0022471 | A1 | 1/2008 | Hilscher et al. |
| 2008/0022501 | A1 | 1/2008 | Hilscher et al. |
| 2008/0022503 | A1 | 1/2008 | Hilscher et al. |
| 2008/0028549 | A1 | 2/2008 | Hilscher et al. |
| 2008/0028587 | A1 | 2/2008 | Renault |
| 2008/0032265 | A1 | 2/2008 | Hilscher et al. |
| 2008/0034515 | A1 | 2/2008 | Hilscher et al. |

FOREIGN PATENT DOCUMENTS

| | | |
|---|---|---|
| CN | 2124686 | 12/1992 |
| CN | 2149877 | 12/1993 |
| CN | 2332378 | 8/1999 |
| DE | 2413524 | 10/1975 |
| DE | 2826008 | 6/1978 |
| DE | 2826008 | 6/1983 |

| | | |
|---|---|---|
| DE | 37 08 801 | 9/1988 |
| DE | 3708801 | 9/1988 |
| DE | 40 36 373 | 11/1990 |
| DE | 39 37 852 | 5/1991 |
| DE | 3936714 | 5/1991 |
| DE | 4012413 | 10/1991 |
| DE | 4036479 | 5/1992 |
| DE | 42 43 219 | 12/1992 |
| DE | 3880015 | 9/1993 |
| DE | 4422086 | 6/1994 |
| DE | 4305013 | 8/1994 |
| DE | 195 06 129 | 2/1995 |
| DE | 195 18 935 | 5/1995 |
| DE | 19618935 | 5/1995 |
| DE | 29608164 | 5/1996 |
| DE | 19627752 | 7/1996 |
| DE | 19506129 | 8/1996 |
| DE | 19628574 | 3/1997 |
| DE | 297 09 865 | 6/1997 |
| DE | 19545324 | 6/1997 |
| DE | 29 608 167 | 9/1997 |
| DE | 299 15 858 | 9/1999 |
| DE | 19832607 | 5/2000 |
| DE | 199 23 104 | 11/2000 |
| DE | 19921677 | 11/2000 |
| DE | 10001502 | 3/2001 |
| DE | 10026513 | 5/2001 |
| DE | 19963651 | 5/2001 |
| DE | 199 53 651 | 10/2001 |
| DE | 10135257 | 2/2002 |
| DE | 10045353 | 3/2002 |
| DE | 10045067 | 4/2002 |
| DE | 10101163 | 7/2002 |
| DE | 10153863 | 5/2003 |
| DE | 10154946 | 5/2003 |
| EP | 024 992 | 6/1984 |
| EP | 0046169 | 8/1984 |
| EP | 0 085 795 | 3/1987 |
| EP | 285 915 | 10/1988 |
| EP | 0300345 | 1/1989 |
| EP | 0435329 | 7/1991 |
| EP | 440 051 | 8/1991 |
| EP | 391 967 | 8/1992 |
| EP | 294 548 | 4/1993 |
| EP | 624 079 | 10/1993 |
| EP | 634 151 | 3/1994 |
| EP | 634 151 | 1/1995 |
| EP | 787 469 | 8/1997 |
| EP | 848 921 | 6/1998 |
| EP | 1267664 | 6/2004 |
| EP | 1379149 | 8/2004 |
| EP | 1244373 | 7/2006 |
| FR | 2832298 | 5/2003 |
| GB | 1167444 | 10/1969 |
| GB | 1246564 | 9/1974 |
| GB | 2082713 | 3/1982 |
| GB | 2117230 | 10/1983 |
| GB | 2146893 | 5/1985 |
| GB | 2376758 | 12/2002 |
| JP | 1989083268 | 3/1989 |
| JP | 04-087127 | 3/1992 |
| JP | 04-269906 | 9/1992 |
| JP | 05-269024 | 10/1993 |
| JP | 08-117030 | 5/1996 |
| JP | 1996187125 | 7/1996 |
| JP | 08-000358 | 9/1996 |
| JP | 08-275961 | 10/1996 |
| JP | 1998005041 | 1/1998 |
| JP | 1998127346 | 5/1998 |
| JP | 1998137040 | 5/1998 |
| JP | 2862873 | 3/1999 |
| JP | 1999113638 | 4/1999 |
| JP | 11-318951 | 11/1999 |
| JP | 2001-37788 | 2/2001 |
| SU | 749380 | 7/1980 |
| SU | 1542539 | 2/1990 |
| SU | 1674789 | 9/1991 |
| WO | WO 91/06258 | 5/1991 |
| WO | WO95/33419 | 12/1995 |
| WO | 97/24079 | 7/1997 |
| WO | 98/24527 | 6/1998 |
| WO | 98/55274 | 12/1998 |
| WO | WO99/20202 | 4/1999 |
| WO | WO99/053562 | 10/1999 |
| WO | 00/74591 | 6/2000 |
| WO | 00/39768 | 7/2000 |
| WO | 00/42584 | 7/2000 |
| WO | 00/47128 | 8/2000 |
| WO | 00/74591 | 12/2000 |
| WO | 01/08591 | 2/2001 |
| WO | WO 01/32052 | 5/2001 |
| WO | WO 01/47392 | 7/2001 |
| WO | 01/91603 | 12/2001 |
| WO | WO0293881 | 1/2002 |
| WO | WO02/083257 | 10/2002 |
| WO | WO02/098315 | 12/2002 |
| WO | WO03/054771 | 7/2003 |

OTHER PUBLICATIONS

U.S. Appl. No. 11/763,338, filed Jun. 14, 2007.
U.S. Appl. No. 11/888,142, filed Jul. 31, 2007.
U.S. Appl. No. 11/888,249, filed Jul. 31, 2007.
U.S. Appl. No. 11/888,251, filed Jul. 31, 2007.
U.S. Appl. No. 11/888,189, filed Jul. 31, 2007.
U.S. Appl. No. 11/888,211, filed Jul. 31, 2007.
U.S. Appl. No. 11/888,212, filed Jul. 31, 2007.
U.S. Appl. No. 11/888,250, filed Jul. 31, 2007.
U.S. Appl. No. 11/888,152, filed Jul. 31, 2007.
U.S. Appl. No. 11/888,287, filed Jul. 31, 2007.
U.S. Appl. No. 11/888,385, filed Aug. 1, 2007.
U.S. Appl. No. 11/888,386, filed Aug. 1, 2007.
U.S. Appl. No. 11/890,083, filed Aug. 1, 2007.
Package rear and bottom panels of Bausch & Lomb Interplak Model PB-6, marked © 1992 (color copy, 1 sheet).
"RFID Made Easy" Handbook by EM Microelectronic-Marin SA, 2074 Marin, Switzerland, corp. 2000 and dated Mar. 2001, Rev. C/350, pp. 1-33.
Office Action from U.S. Appl. No. 09/811,080 dated Oct. 1, 2004 (8 pages).
Office Action from U.S. Appl. No. 09/811,080 dated Feb. 3, 2004 (19 pages).
Office Action from U.S. Appl. No. 10/241,274 dated Jan. 14, 2005 (4 pages).
Office Action from U.S. Appl. No. 10/241,274 dated Sep. 1, 2006 (14 pages).
Office Action from U.S. Appl. No. 10/662,237 dated Feb. 18, 2005 (6 pages).
Office Action from U.S. Appl. No. 10/872,016 dated Feb. 7, 2006 (17 pages).
Office Action from U.S. Appl. No. 10/872,016 dated Feb. 23, 2007 (12 pages).
Office Action from U.S. Appl. No. 10/872,016 dated Mar. 7, 2008 (22 pages).
Office Action from U.S. Appl. No. 10/872,016 dated Jun. 24, 2005 (20 pages).
Office Action from U.S. Appl. No. 10/872,016 dated Jul. 10, 2006 (4 pages).
Office Action from U.S. Appl. No. 10/872,016 dated Aug. 7, 2007 (4 pages).
Office Action from U.S. Appl. No. 10/872,016 dated Sep. 20, 2006 (12 pages).
Office Action from U.S. Appl. No. 10/872,016 dated Nov. 5, 2008 (14 pages).
Office Action from U.S. Appl. No. 10/872,075 dated Dec. 27, 2006 (11 pages).
Office Action from U.S. Appl. No. 10/872,075 dated Oct. 31, 2007 (8 pages).
Office Action from U.S. Appl. No. 10/872,075 dated Mar. 24, 2006 (19 pages).
Office Action from U.S. Appl. No. 10/872,075 dated Apr. 11, 2008 (4 pages).
Office Action from U.S. Appl. No. 10/872,075 dated May 15, 2007 (9 pages).

Office Action from U.S. Appl. No. 10/872,075 dated Aug. 1, 2006 (15 pages).
Office Action from U.S. Appl. No. 10/872,075 dated Dec. 10, 2008 (15 pages).
Office Action from U.S. Appl. No. 11/257,603 dated Jan. 18, 2007 (7 pages).
Office Action from U.S. Appl. No. 11/257,603 dated Mar. 21, 2008 (21 pages).
Office Action from U.S. Appl. No. 11/257,603 dated May 15, 2007 (6 pages).
Office Action from U.S. Appl. No. 11/257,603 dated Aug. 30, 2007 (12 pages).
Office Action from U.S. Appl. No. 11/257,603 dated Sep. 20, 2006 (6 pages).
Office Action from U.S. Appl. No. 11/257,603 dated Nov. 25, 2008 (16 pages).
Office Action from U.S. Appl. No. 11/763,338 dated Jul. 10, 2008 (20 pages).
Office Action from U.S. Appl. No. 11/888,212 dated Mar. 21, 2008 (6 pages).
Office Action from U.S. Appl. No. 11/888,250 dated Jun. 3, 2008 (6 pages).
Office Action from U.S. Appl. No. 11/888,251 dated Mar. 21, 2008 (7 pages).
PCT Search Report in PCT/EP 01/02844 dated Aug. 8, 2001 (3pp.) corresponding to U.S. Appl. No. 10/662,237.
PCT Search Report in PCT/EP 01/02862 corresponding to U.S. Appl. No. 09/811,080, dated Jul. 31, 2001.
PCT Search Report in PCT/EP 02/01724 dated Jul. 17, 2002 (3pp.) corresponding to U.S. Appl. No. 10/241,274.
U.S. Appl. No. 09/811,080, filed Mar. 16, 2001.
U.S. Appl. No. 11/257,603, filed Oct. 24, 2005.
U.S. Appl. No. 11/763,338, filed Jun. 14, 2007.
Office Action from U.S. Appl. No. 11/763,338 dated Dec. 4, 2008 (20 pages).
USPTO Office Action in U.S. Appl. No. 10/872,016, mailed Apr. 10, 2009, 11 pages.
USPTO Office Action in U.S. Appl. No. 10/872,075, mailed Jun. 4, 2009, 19 pages.
USPTO Office Action in U.S. Appl. No. 11/763,338, mailed Mar. 24, 2009, 20 pages.
USPTO Office Action in U.S. Appl. No. 11/888,212, mailed Mar. 17, 2009, 11 pages.
USPTO Office Action in U.S. Appl. No. 11/888,251, mailed Mar. 17, 2009, 22 pages.
USPTO Office Action in U.S. Appl. No. 11/888,386, mailed Mar. 3, 2009, 24 pages.
USPTO Office Action in U.S. Appl. No. 11/890,083, mailed Mar. 16, 2009, 35 pages.
Color Photographs of Bausch & Lomb "Interplak" Model PB-4B Style Hand piece with Travel Protection Switch and Toothbrush Attachment (hand piece stamped "1D 1A", believed circa 1992 on sale in the US) (2 sheets with 7 views).
Package Rear and Bottom Panels of Bausch & Lomb Interplak Model PB-4B, marked © 1990 (color copy, 1 sheet).
Applicants application U.S. Appl. No. 10/662,237, filed Sep. 15, 2003 believed pending, published on Jun. 10, 2004.
Product use instructions to Bausch & Lomb Interplak travel-style "Voyager" Model TK-2 marked ©1991 (6 photocopied sheets containing cover and pp. 1-10).
Color photographs of Bausch & Lomb "Interplak" Model PB-6 Style Hand-piece with waterproof electronic travel protection switch (believed circa 1992 on sale in U.S.) (6 views on 1 page).
Package Rear and Bottom Panels of Bausch & Lomb Interplak Model PB-6, marked © 1992 (color copy, 1 sheet).
"RFID made easy" Handbook by EM Microelectronic-Marin SA, 2074 Marin, Switzerland, copr. 2000 and dated Mar. 2001, Rev. C/350, pp. 1-33.
Finkenzeller, Klaus, "RFID-Handbuch, Grundlagen und praktische Anwendungen induktiver Funkanlagen, Transponder und kontaktloser Chipkarten" [Trans: "RFID Handbook. Fundamentals and practical Applications to inductive radio Communications, Transponders and Contactless Chip Cards"], Carl Hanser Verlag Munchen, 2nd Edition, Chapter 3, pp. 29 to 58 with title page and Impressum.Contents pp. vii-xviii, -and Appendices 15.2 "Standards" and 15.3 "Literature" on pp. 393 to 406.
Herzer, Gieselher, "Der grosse Lauschangriff auf Ladendiebe" [transl. "The great surveillance of Shoplifters"] in Physikalische Blaetter [transl.: Physics Letters} vol. 57 (2001), No. 5, pp. 43-48.

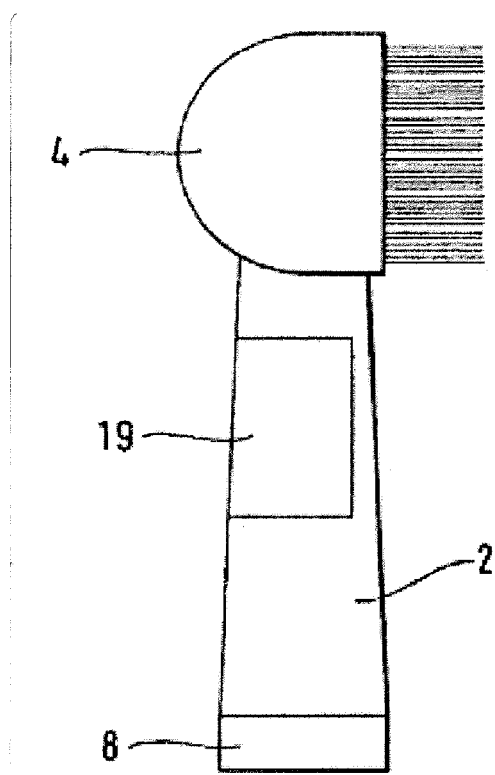
Fig. 18
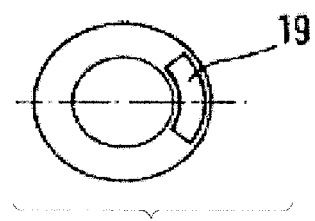
Fig. 18A
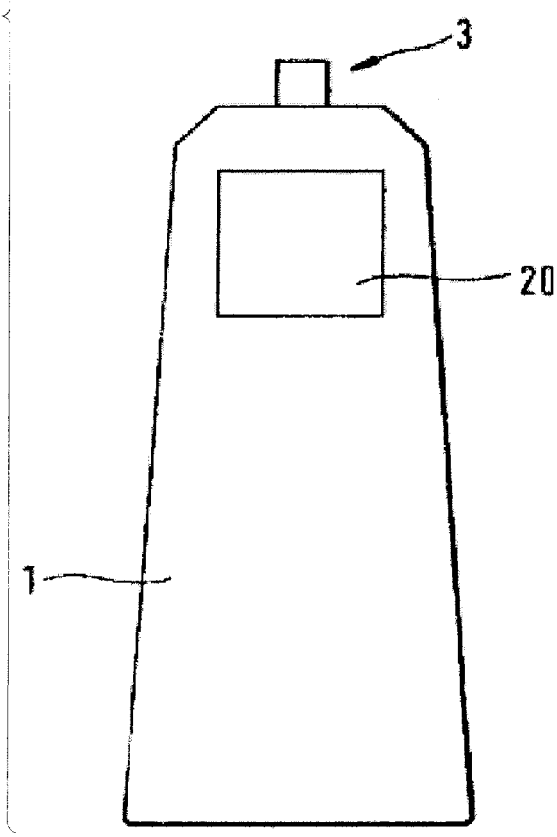

DENTAL CLEANING DEVICE

This application is a continuation of U.S. application Ser. No. 10/871,469, filed on Jun. 18, 2004, now U.S. Pat. No. 7,624,467, issued Dec. 1, 2009, which is a continuation of U.S. application Ser. No. 09/811,080, filed on Mar. 16, 2001, now U.S. Pat. No. 7,086,111, issued Aug. 8, 2006. Each of these applications is incorporated by reference in its entirety.

This invention relates to an electric dental cleaning device. The invention relates in particular to the handle section of such a dental cleaning device which has at least one or several coupling sections for the coupling of various cleaning tools, a drive mechanism for driving the coupled cleaning tool, and a control device. Finally the invention relates to the cleaning tools, particularly brush attachments for such a handle section.

Dental cleaning devices such as electric toothbrushes or electric oral irrigators customarily have a grip or a handle section or handhold to which a variety of cleaning tools such as brush attachments, jet nozzles, interproximal brushes are attachable, thus enabling several users to use the dental cleaning device with their own, in particular person-related cleaning tools. Such electric toothbrushes are known, for example, from DE 19627752 A1 or EP 0624079 B1.

From DE 299 15 858 U1 a dental cleaning device is known in which each of the different toothbrushes can be inserted only into its assigned receptacle in a console. This then starts the program provided for this particular toothbrush. Particularly children find it however difficult to locate the individual opening for insertion of their personal toothbrush and to mate the plug there. Furthermore, this console involves high complexity of manufacture, considering that it requires the provision of a plurality of different receptacles and each of the toothbrushes has a different plug assigned to its own receptacle.

In a further device disclosed in U.S. Pat. No. 5,184,959, each hand toothbrush is assigned its own accommodating slot in a housing, so that each toothbrush can be assigned an individual brushing time signal via the housing. This arrangement is very elaborate from the manufacturing point of view without providing for the detection and storage of user-specific data of the tooth cleaning operation.

Such dental cleaning devices are capable of improvement on many counts. One problem is in particular that in storage-battery-operated toothbrushes the storage battery may become depleted prematurely. This may happen, for example, in cases where the toothbrush is not properly stowed away in a travel bag or the like, so that the drive mechanism turns on accidentally. Furthermore, it may happen that the handle section is not always coupled with the correct brush attachments, so that as a result of the lack of compatibility the handle section, for example, the coupling sections, may be damaged particularly in the area of the drive train, or a proper cleaning function is not assured, likewise for lack of compatibility.

It is therefore an object of the present invention to provide an improved handle section of an electric dental cleaning device and improved cleaning tools therefor, which avoid the disadvantages of the prior art, develop it further and afford additional advantages. In particular the invention aims to provide a comfortable safety device preventing accidental activation and/or improper use of the dental cleaning device.

According to the invention the object referred to in the foregoing is accomplished in a handle section of an electric dental cleaning device of the type initially referred to essentially in that a control device of the handle section possesses an interlock device which can be deactivated by an interlock canceling element provided on the cleaning tool. With regard to the cleaning tool of the type initially referred to, this object is accomplished in that it possesses an interlock canceling element for deactivating the interlock device of the handle section. Preferred embodiments of the invention are the subject-matter of dependent claims.

These solutions hence afford protection against accidental activation of the dental cleaning device. The drive mechanism of the handle section can be turned on only when a compatible cleaning tool is attached to the handle section, whereupon the interlock device is deactivated. Accidental turning on in the travel case can be prevented simply by detaching the cleaning tool from the handle section. Any inadvertent premature discharge of a storage battery is not possible either. Additional provisions in terms of the design or mechanics for implementation of the interlock, for example, on the switch of the handle section, are unnecessary.

In a further aspect of the invention provision may be made for the interlock device to be deactivatable exclusively by the interlock canceling element of the cleaning tool, in particular only when the cleaning tool is properly coupled to the handle section. This is accomplishable in that the interlock canceling element provided on the cleaning tool and a detection device provided on the handle section for detecting the presence of the interlock canceling element are constructed and in relative agreement in such manner that the interlock canceling element is effective preferably in a predetermined orientation and/or position relative to the detection device and hence to the handle section.

To prevent the handle section, in particular the drive train or its coupling device from being damaged by the attachment of incompatible brush attachments, the interlock canceling element may be configured as an encoding identifying the cleaning tool. The handle section then includes an encoding detection device detecting the encoding of the attached cleaning tool. The interlock device is deactivated only when the encoding detection device reads the proper encoding and generates a corresponding signal. Hence the handle section detects the cleaning tool attached thereto and controls, in response to the detected cleaning tool, the release of the drive mechanism.

It will be understood that the encoding detection device may sample an encoding of the cleaning tool at predetermined intervals. In a particular configuration of the invention the encoding detection device is activated only when an on-switch of the handle section, for example, of the electric drive mechanism, is actuated. This has the advantage that the current consumption of the encoding detection device is kept at a minimum level. To turn the dental cleaning device on, the user actuates the on-off switch of the control device or of the electric motor as usual. Actuation of the switch, however, does not set the electric motor, meaning the drive mechanism, in operation directly, but initially activates only the encoding detection device which, upon establishing that a compatible brush attachment, i.e., a brush attachment with the proper encoding, is coupled to the handle section, then sets the motor of the handle section in operation. Ultimately, therefore, an activation of the encoding detection device by means of the on-off switch sets the drive mechanism of the handle section in operation only indirectly, that is, when the interlock canceling element of the brush section deactivates the interlock device of the handle section. In the absence of a brush section attached or coupled to the handle section or in the event of an incompatible brush section fitted to the handle section, the encoding detection device, upon actuation of the on-off switch, will fail to detect a proper encoding, or the absence of the interlock canceling element on the brush attachment will prevent the interlock device on the handle section from being deactivated, so that in this case the handle section of the electric-motor-operated toothbrush cannot be set in operation. Among other advantages, this approach involving activation of the encoding detection device by means of the on-off switch has the advantage that power supply to the encoding detection device is necessary preferably only during operation of the on-off switch of the handle section, while being otherwise inactive or passive. It will be understood, of course, that it is also possible for the encoding detection device to be activated at regular or irregular intervals during operation of the toothbrush in order to check the presence of a compatible, that is, properly encoded brush attachment also during periods other than the on-off switching period. When the on-off switch is actuated again on termination of the dental cleaning operation to turn off the drive of the handle section, this will stop the drive promptly and, where provided, will deactivate the interlock device, so that when the on-off switch on the handle section is switched on again subsequently the described cycle can be repeated.

A variety of approaches are possible for detection of the encoding provided directly on the cleaning tools or the signals of the interlock canceling element and for the encoding or configuration of the interlock canceling element of the cleaning tools.

In particularly simple manner the cleaning tool is encoded by its shape. It may possess one or several shaped bodies which are connected to the body of the cleaning tool in particular fixedly and lie in the range of detection of the encoding detection device of the handle section when the cleaning tool is coupled to the handle section. The encoding may embody a specific geometrical contour, for example, outer contour, and/or a specific spatial arrangement of the shaped body relative to the coupling section of the cleaning tool and hence also to the encoding detection device on the handle section. Detection of the shaped body or bodies may be performed in non-contacting fashion using, for example, light barriers or the like.

In an embodiment of the invention the encoding of the individual cleaning tool is brought into mechanical contact with the encoding detection device, enabling it to read the encoding. This results in a particularly straightforward construction.

The handle section may include a scanning device for scanning the encoding provided on the respective cleaning tool being used, that is, for deactivating the interlock.

Preferably the handle section may include a movable or deformable sensing element which is moved, deformed or otherwise acted upon by the mechanical encoding of the cleaning tool as the latter is being seated onto the handle section. Depending on the encoding, the sensing element is moved or displaced or deformed by a predetermined amount or in a predetermined direction. The sensing element produces a signal responsive to the movement or deformation so that the encoding can be detected. The sensing element may also be configured in such manner that it senses a force or a field, for example, an electromagnetic field, which is generated by the encoding and acts upon the sensing element as the cleaning tool is being seated onto the handle section, causing the sensing element to deliver actively a signal. To obtain a particularly simple configuration the sensing element may be constructed as a preferably electromechanical contact member. This member, upon being correspondingly deformed or moved by the encoding of the cleaning tool, then opens or preferably closes one or several contacts so that a corresponding signal is produced.

The sensing element may be configured in such a manner that it is deformed to different degrees or moved in different directions responsive to the encoding of the attached cleaning tool, correspondingly closing different contacts or a different number of contacts.

In a further aspect of the invention provision is made for several sensing elements so that different encodings of the cleaning tools cause different sensing elements or a different number of sensing elements to be actuated.

The sensing element(s) may be arranged so as to be freely accessible. In this arrangement the sensing element may be brought into operative association directly with a corresponding encoding element of the cleaning tool. In an advantageous embodiment of the invention the sensing element is indirectly actuatable. The sensing element may be disposed in the interior of a housing of the handle section which may have a deformable portion, for example in the form of a soft plastic portion, through which the sensing element can be actuated. This enables a sealed, in particular fluid-tight construction of the handle section to be obtained.

In another advantageous embodiment of the invention the encoding detection device may include a movable probe element which is moved by the encoding of the cleaning tool during its seating engagement with the handle section. The encoding detection device includes a motion sensor detecting the movement or displacement of the probe element advantageously in terms of amount and/or magnitude. The encoding of different cleaning tools may be uniform or, alternatively, different so as to effect movements or displacements of the probe element of different magnitude and/or in different directions as the cleaning tool is being attached to the handle section. Provision may be made for several probe elements so that individual probe elements or different combinations of probe elements can be actuated by differently arranged encoding sections of the cleaning tools.

Various configurations are possible for the motion/displacement sensor. It may operate optically, for example, in the manner of a light barrier. It may also detect the force exerted on the probe element by an encoding. Preferably a sensing element of the type described in the foregoing may find application which in this case is actuated indirectly, that is, through the probe element.

A particularly advantageous embodiment of the invention resides in that the probe element is the drive shaft of the drive mechanism arranged in the handle section for driving the cleaning tool. The drive shaft may be mounted in the handle section in longitudinally displaceable fashion so that it is pushed into the interior of the handle section a certain amount by the encoding of the cleaning tool as it is being seated onto the handle section. The use of the drive shaft as probe element obviates the need for any specific additional arrangements with regard to the sealing of the handle section because the drive shaft is invariably sealed. In this embodiment it proves however necessary for the attachment, in particular the brush attachment, to be held on the handle section in a defined end position when in coupled condition. This is accomplishable, for example, by providing in or on the coupling shank of the handle section detent elements such as grooves, projections or the like which cooperate with corresponding mating detent elements as, for example, the tube of the attached cleaning tool and ensure, by such cooperation, that the brush attachment can be coupled to the handle section only in an accurately defined position. This position is selected such that when an attachment is in this defined coupling position the drive shaft is displaced axially toward the handle section by a predetermined amount, this displacement being used, for example, to actuate a switch or the like. The prerequisite for this is, of course, that the attachment includes elements registering with the drive shaft or the shaft's free end, as, for example, abutments, bearing surfaces, activating elements, which on seating of the brush attachment onto the handle section and bringing it into the defined end position produce a defined axial displacement of the drive shaft so that this displacement of the drive shaft enables the actuation of associated switches or other sensors arranged in the interior of the handle section, this arrangement being hence likewise suitable for detecting the presence of a coupled brush attachment on the handle section provided that the brush attachment is a compatible replacement brush or some other replacement cleaning tool suited or permitted for use with the handle section.

As encoding the cleaning tool preferably has an actuating surface, in particular a pressure application surface, an abutment or some other activating element which is constructed and arranged such as to make engagement or contact with an engagement surface of the encoding detection device when the cleaning tool is seated onto the handle section, exerting a defined effect on said surface. The actuating surface and the engagement surface thus form interacting surfaces. Provision may be made for actuating surfaces of different encoding to exert different effects on the same engagement surface, moving it, for example, a greater or lesser amount. Provision may further be made for different actuating surfaces to act on different engagement surfaces, thereby enabling the encoding to be read. The engagement surface on the handle section may be disposed directly on the sensing element previously described or, alternatively, on the probe element likewise described in the foregoing, in particular on the drive shaft of the handle section. In the last mentioned instance the actuating surface is preferably provided on a drive shaft section of the drive shaft provided in the cleaning tool. This arrangement is particularly advantageous because it makes use of the existing coupling sections provided for the coupling of cleaning tool and handle section, which coupling sections, suitably modified, detect the respective cleaning tool, thus obviating the need to provide additional mechanical elements for this purpose. The coupling section on the cleaning tool is suitably encoded by means and in the form of an actuating surface to exert a defined effect, particularly a defined actuating motion, for example, a defined stroke, on the coupling section on the handle section which for this purpose is provided with a corresponding engagement surface.

In another advantageous embodiment of the invention the encoding detection device is of the noncontacting type. This has the advantage of avoiding malfunctions due to contaminated contact surfaces or wear resulting from frequent attachment and disengagement operations.

According to a further aspect of the invention the handle section may include a signal receiver for receiving from the cleaning tool an encoded signal or an interlock deactivating signal. The handle section may also possess a signal transmitter emitting an interrogation or activation signal to the cleaning tool which responds by sending the encoded signal or the interlock deactivating signal back. The emission of the encoded signal or interlock deactivating signal by the cleaning tool may take place actively by a corresponding signal transmitter or a suitable acting member, as a magnet or the like. The possibility also exists for passive reflection to take place on the cleaning tool, which produces a corresponding encoding of the signal or an interlock deactivating signal.

The encoding or configuration of the interlock canceling element of the cleaning tools and the corresponding detection of the encoding or interlock canceling element may be implemented in a further variety of ways. According to a preferred embodiment of the invention provision is made for a magnetic sensor detecting a magnetic encoding or a magnetically effective interlock canceling element of the respective cleaning tool attached to the handle section. The magnetic encoding or configuration of the interlock canceling element of the cleaning tool(s) may take place by introducing a uniform or, where provided, individually different number of magnetic particles or a preferably small magnetic, for example, a bar magnet or some other permanent magnet into the cleaning tool itself or in a portion or part of the cleaning tool, for example, in a colored ring or profiled ring as represented, for example, in WO 99/20202, which shall be deemed to be incorporated in the disclosure content of the present application by express reference. The sensor for detecting the magnet, meaning the magnetic field, of the cleaning tool may also be of different configurations. According to a preferred embodiment of the invention the handle section includes, preferably in the upper section of the area of coupling with the attachable cleaning tool, a Hall sensor providing an electrical signal corresponding to the magnetic encoding or to the one uniform magnet of the interlock canceling element of the respective cleaning tool. According to a further preferred embodiment of the invention the handle section may include an LC oscillator which is detuned by the magnetic encoding or the magnet of the attached cleaning tool, thus supplying different frequencies assignable to the individual users for purposes of deactivating the interlock of the handle section.

Another advantageous embodiment of the invention resides in the provision of one or several reed contacts on the handle section which are actuated in particular individually when the cleaning tools are attached to the handle section. Depending on the combination of contacts actuated, an interlock deactivating signal may be generated or not. In accordance with an advantageous embodiment of the invention provision may be made for an optical sensor for detecting an optical encoding of the respective cleaning tool attached to the handle section. As optical encoding a color code may be provided on the cleaning tool which is identified by a color sensor.

Advantageously the handle section may also be equipped with one or several optical waveguides exiting from the handle section and emitting an optical signal. The light signal delivered to the cleaning tool is encoded by the tool and returned to the handle section which receives this encoded signal by means of a corresponding sensor or detector and converts it, receiving it by means of corresponding optical waveguides and transmitting it to a corresponding sensor. The encoding may take place by defined interruption or partial obstruction of the optical waveguides exiting from the handle section. Moreover, the light exiting from the handle section through the optical waveguide can be reflected differently by the toothbrush. The interlock device can be deactivated in response to the intensity of reflection.

According to another preferred embodiment of the invention provision may be made for a capacitive sensor for detecting a capacitive encoding, meaning the presence of the interlock canceling element of the respective cleaning tool attached. In particular the handle section may have two or more capacitor plates whose capacitance is varied by the introduction of a dielectric provided on the cleaning tool. The encoding of the cleaning tools may be performed by different dielectric portions on the respective cleaning tool. A particular or compatible cleaning tool is then detectable in accordance with the variation in capacitance.

In a further advantageous embodiment of the detection device provision is made for an electrically operating sensor for detecting an electrical encoding, meaning the presence of the interlock canceling element of the respective cleaning tool attached. The cleaning tool sends an encoded electrical signal to the handle section, meaning to a signal receiver provided thereon, thus enabling the respective cleaning tool to be identified. It is also possible for the handle section to send initially an interrogation signal to the cleaning tool which is encoded by the cleaning tool and subsequently sent back.

In a further aspect of the invention provision may be made for a transmit or radio device for detecting the respective cleaning tool attached by means of electromagnetic waves. In particular a transponder may be associated with the cleaning tool. The handle section initially emits electromagnetic waves for energy supply to the transponder. The transponder stores the energy and sends an individual identification back to a detector in the handle section which detects it and correspondingly identifies the cleaning tool and deactivates the interlock.

The characteristic features of the cleaning tool thus include a magnetic, electrical, optical, capacitive, electromagnetic and/or mechanical encoding device or such an interlock canceling element. Another characteristic feature may include a signal receiver for receiving a signal from the dental cleaning device and a signal transmitter for transmitting an encoded signal to the dental cleaning device, with an encoding device being inserted between the signal receiver and the signal transmitter for encoding the received signal.

The encoding device or interlock canceling element is preferably constructed as a separate component suitable for detachment from the remaining part of the cleaning tool or for replacement. This affords the advantage of requiring only a single mold for the manufacture of the cleaning tool. By mounting the separate encoding device the cleaning tools are encoded on an individual basis and assignable to a handle section of a particular type. However, the encoding device constructed as interlock canceling element may also be integrated in the cleaning tool when it is desirable to implement merely the function of a safety interlock preventing switching on of the appliance on travels or in combination with incompatible cleaning tools.

The encoding device is arranged preferably in the area of the connection or coupling between the cleaning tool and the handle section. This facilitates the reading of the encoding, meaning the detection of the interlock canceling element by the recognition device on the handle section. In particular the encoding device may be integrated in a ring arranged at the end of the cleaning tool close to the handle section, being in particular snap-fittable thereto by positive engagement therewith. The various configurations of the recognition devices may be provided singularly or in combination. The same applies to the various configurations of the encoding device on the cleaning tool.

Apart from protecting the handle section against inadvertent turning on and improper use of incompatible cleaning tools, an encoding of the cleaning tools and its detection by the handle section may be utilized to advantage for implementing further functions. In a further aspect of the invention the handle section may control one or preferably several functions of the dental cleaning device in dependence upon the respective cleaning tool detected. Assuming that each user of the handle section has his or her own cleaning tool, particularly the control device of the handle section may establish automatically, by referring to the detected encoding on the cleaning tool, which user is currently using the dental cleaning device. There is no need on the user's part to inform the dental cleaning device of its current user as by pressing a button and the like. An adaptation to the individual user can take place automatically. This results in a maximum of user friendliness.

In particular in a further feature of the invention the control device is capable of adapting operating parameters such as brushing frequency, brushing speed and brushing time or threshold value or desired range of application pressure automatically to the individual user identified. A variety of user profiles can be set and stored, one of which is used by the control device after, at the beginning of brushing, the encoding of the cleaning tool being used has been detected and the respective user has been established. To this effect the encoding detection device has issued a corresponding signal to the control device. Where electric toothbrushes are used, it is possible for example for the motor speed to be reduced from the usual speed for adults when a child is the user, so that a gentler cleaning operation is performed for the child. In addition, the control device may vary, responsive to a signal from the encoding detection device, the duration of a timer according to the user identified, setting the timer to two minutes for children and to three minutes for adults, for example. The type of timer signal could also be modified, as by selecting a tune for children and a buzzer tone for adults.

In a further aspect of the invention it is also possible to store, process and indicate as on a display user-specific data such as brushing frequency, brushing speed, brushing time, time interval between brushing operations or application pressure automatically in response to a corresponding signal from the detection device. This too results in enhanced user comfort.

The handle section then detects, i.e., identifies, the individual user indirectly by referring to the cleaning tool used or its encoding. Each user is assigned to a cleaning tool of his or her own. For this purpose the cleaning tools, which otherwise may be of identical construction, may have user-specific encoding elements.

Provision may also be made for a specific function control in dependence upon the particular type of cleaning tool used. For instance, operating parameters of the handle section may be varied automatically when a brush attachment with specific properties such as high or low hardness is used. Equally, an other operating program may be run when a cleaning tool of different type as, for example, an inter-proximal cleaning tool, a tool for gum massage or a tongue scraper is attached to the handle section. Rotational speed, desired cleaning time, driving motion, cleaning frequency, cleaning speed, application pressure threshold value, etc. can be suitably adapted in response to the individual and/or person-related exchangeable cleaning tool.

Still further, by identifying an individual cleaning or brushing tool or refill unmistakably it is possible to establish its state of wear precisely, for example, by evaluating the history of this particular cleaning tool, in particular the time of past uses. Where cleaning tools with chemical additives are used, their "use by" date can be identified by the date of manufacture hidden in the encoding. Predetermined cleaning or maintenance intervals can be indicated.

In summary, the gist of the present invention shall be presented as follows, also independently of the wording in the claims: The interlock canceling element on the cleaning tool for deactivation of the interlock device can be configured in the simplest configuration of the encoding detection device in such manner that only the presence or absence of a replacement brush on the handle section is detectable. To this effect, for example, an acting member may be arranged in the brush which corresponds with a reacting member disposed in the handle section in such manner that with the cleaning tool and the handle section in coupled condition the reacting member receives from the acting member a signal and deactivates, for example, the interlock device, thus enabling the handle section and hence also the cleaning tool to be set in operation by means of the drive mechanism. This provides a simple design of a travel safety device for the handle section preventing the handle section from operating when the cleaning tool with its acting member is not coupled thereto as described above. Accordingly it is sufficient to decouple the cleaning tool from the handle section to activate the travel interlock. Further steps for locking, for example, the on-off switch of the handle section or any other devices are not necessary. It is also helpful to arrange such an acting member in the cleaning tool which in coupled condition corresponds or communicates with a reacting member in the handle section so that operation of the handle section with incompatible cleaning tools can be prevented, because the manufacturer does not equip such incompatible cleaning tools with an acting member capable of communicating with the reacting member of the handle section. This represents an encoding detection device in its simplest form, it is of relatively straightforward construction and permits merely a decision to be made as to whether a cleaning tool is coupled to the handle section or whether a compatible cleaning tool is coupled to the handle section.

For exceptional situations provision may also be made for the acting member typically provided in the cleaning tool, for example, a magnet or the like or the encoding device to be made available to the end user as a separately handleable isolated part or to provide it on the handle section itself. This approach offers itself, for example, when the end user is already in possession of a handle section equipped with an interlock device but has a household supply of brushing or cleaning tools available which are not equipped with an interlock canceling element or an acting member for deactivation of the interlock of the handle section or handhold. To assure usability of these typically older replacement cleaning tools which, while being mechanically compatible with the more recent handhold, do not have as yet an interlock canceling element which would be suited for communication with, and deactivation of, the interlock device provided in the handle section, a meaningful approach may therefore be to make the interlock canceling element or the acting member available to the end user as a separately handleable component, providing for these exceptional situations a fastening device on the handle section to fasten the interlock canceling element there. This enables, for example, the end user to fasten this interlock canceling element or acting member directly to the handle section or handhold equipped with the interlock device, as on the exterior of the housing in the area of the reacting member of the handle section, and to deactivate for such special or exceptional cases the interlock device on the handle section by arranging the acting member on the handle section itself and not on the cleaning tool. As a result, the handle section is also operable with cleaning tools which, while being mechanically compatible, are not as yet equipped with an interlock canceling element or an acting member communicating with the interlock device. This solution may also be contemplated when for cost reasons, for example, not all of the replacement cleaning tools compatible or mechanically mating with the handle section or handhold are equipped with such an interlock canceling element, an encoding device or an acting member. It will be understood, of course, that the solution involving the fastening of the interlock canceling element directly to the handle section as by its user is an exceptional situation, and that as a rule the interlock canceling element should be arranged on the brush section or cleaning section. Particularly in the event of the interlock canceling element being a magnetic field effecting member having associated with it a reacting member in the handle section or handhold which is responsive to magnetic fields, a solution offering itself for this exceptional case may involve magnetization of the handle section's drive shaft, which is typically disposed in close proximity to the reacting member, for deactivation of the interlock device of the handle section, or to provide a magnetic adhesive strip or the like which may be adhered to the handle section at a suitable location in the area of the reacting member. This approach, too, enables deactivation of the interlock device and operation of the handle section or handhold with compatible cleaning tools having no interlock canceling element.

Still further, the encoding detection device may also be configured so as to enable the coupling of a cleaning tool allowing for a few possibilities of distinction of cleaning tools. While the encoding detection device initially described permits, for example, only a yes/no decision, that is, a decision as to whether or not a compatible cleaning tool is coupled to the handle section, a modified encoding detection device permitting, for example, the identification of two, four or six different encodings of the cleaning tool enables further functions to be implemented in addition to the travel safety function. Thus, for example, it is possible for the handle section to identify whether a toothbrush designed for adults (hard bristles) or a toothbrush designed for children (soft bristles) is coupled to the handle section, whether an interproximal cleaning device is used in lieu of a toothbrush, or also to distinguish between other parameters. Where provided, the detected encoding can be used for an individual actuation of the control device for the drive including, for example, a control of the speed of the drive as the rotational speed or the desired brushing time or the like. In the event of provision being made for an encoding or an encoding detection device with few (between about two and about ten) possibilities of distinction, it is however not possible as yet to identify an individual cleaning tool from a million of commercially available cleaning tools. With these limited possibilities of distinction it is at best possible to identify a special type of cleaning tool (child toothbrush, adult toothbrush, interproximal brush, dental flossing device, each configured as an attachment to the handle section) and to make a distinction between a few person-related cleaning or brushing tools.

When it is desired to detect with the encoding detection device every single individual cleaning tool produced by the manufacturer which is adapted to be coupled to the handle section as a compatible part, allowance need be made for a multiplicity of possibilities of distinction in the range from about $10^6$ to about $10^{12}$, for which purpose a transponder or similar electronic device is typically used. In this case identification of an individual cleaning tool supplied by the manufacturer and coupled to the handle section is possible. In addition to the possibilities already mentioned in connection with simpler encodings, this provides the prerequisite for the ability to determine, for example, the degree of wear of the cleaning tool more accurately by evaluating the tool history. Where replacement cleaning tools with chemical additives are used, the date of manufacture indicated in the encoding enables "use by" dates to be identified or predetermined cleaning or maintenance intervals of the cleaning tool to be indicated or complied with.

Regardless of how simple or complicated the encoding of the cleaning tool and the encoding detection device, each of these encodings is suitable for providing a travel safety function by decoupling the in particular compatible cleaning tool from the handle section, thereby preventing operation of the handle section. Setting the handle section in operation is likewise prevented with any one of these encodings, whether of simple or elaborate design, if the cleaning tool does not have an encoding or interlock canceling element in the first place. When such a cleaning tool which is not encoded or not equipped with an interlock canceling element is coupled to the handle section, the reacting member, transmitter, receiver or similar device positioned in the handle section is unable to communicate with the acting member, transmitter, receiver, transponder or similar device not provided in the incompatible cleaning tool, so that precisely as in the case of a cleaning tool which is compatible but not coupled to the handle section, the presence of this incompatible cleaning tool is not recognized on the handle section, as a result of which the handle section cannot be set in operation due to the absence of the interlock canceling element and the attendant lack of possible deactivation of the interlock device.

In the basically most straightforward form of construction of the encoding of the cleaning tool or the encoding detection device in the handle section of the electric toothbrushing device, care has to be taken only to ensure that the encoding detection device in the handle section is in a position to recognize whether or not a proper, i.e., compatible cleaning tool is coupled to the handle section. If such a proper, i.e., compatible cleaning tool is not coupled to the handle section, the handle section cannot be set in operation, because the cleaning tool has no associated interlock canceling element suitable for deactivation of an interlock device provided in the handle section. By contrast, when a compatible cleaning tool equipped with the interlock canceling element or the proper encoding is coupled to the handle section, it is not later than on actuation of the on-off switch on the handle section that the presence of the proper encoding or interlock canceling element will be detected by means of a detection device in the handle section, causing deactivation of the interlock device and setting the handle section in operation, so that the cleaning end, for example, the brush head of the cleaning tool, is set in operation by the drive mechanism of the handle section.

Insofar, the present invention also relates to a method of operating an electric tooth cleaning or tooth brushing device comprised of a handle section and a cleaning tool adapted to be attached or coupled thereto, as for example, a brush attachment or the like, wherein the handle section and the cleaning tool communicate with each other in coupled condition, devices being provided in the handle section which are in a position to detect whether a cleaning tool is coupled to the handle section and/or whether the cleaning tool coupled to the handle section is a cleaning tool compatible with the handle section. When no cleaning tool is coupled to the handle section, this information is used for suppressing an activation of the electric drive of the handle section, which could take place, for example, by means of the on-switch provided on the handle section. This may be accomplished, for example, by an interlock device in the handle section. Hence it is not possible to set the handle section in operation with the cleaning tool not coupled or attached thereto, whereby a comfortable travel safety device is obtained. A further feature characteristic of the method is that the cleaning tool includes an interlock canceling element signaling to a detection device arranged in the handle section that the cleaning tool is coupled to the handle section and the interlock device can be deactivated, meaning canceled, to enable the dental cleaning appliance to be set in operation by turning on the electric drive. If however the cleaning tool is not equipped with such an interlock canceling element, even in coupled condition of cleaning tool and handle section the drive of the handle section cannot be activated because in the absence of an interlock canceling element on the cleaning tool it has to be assumed that a cleaning tool incompatible with the handle section is involved.

Further embodiments of the method also include the step of encoding the different cleaning tools to be coupled to the handle section on a person-related, cleaning-tool-related or similar basis, enabling the handle section or handhold to be informed, via a corresponding encoding detection device, not only of the coupled or non-coupled condition of a cleaning tool or a compatible cleaning tool but also of the type of cleaning tool used or the individual using the cleaning tool, so that corresponding parameters or also operating parameters of the handle section can be set or stored as person- and/or cleaning-tool-related data. These individual approaches are explained in detail within the scope of the description of the device and also pertain to the present method as features essential to the present invention. It will be understood that within the scope of the present invention the terms interlock device and encoding detection device or recognition device as well as the terms interlock canceling element and encoding device or encoding element are used as synonyms and may be used interchangeably in each individual case without departing from the scope of the invention.

Further objects, advantages, features and application possibilities of the present invention will become apparent from the subsequent description of embodiments illustrated in the accompanying drawings. It will be understood that any features described and/or represented by illustration, whether used singularly or in any meaningful combination, form the subject-matter of the present invention, irrespective of their summary in the claims or their back reference.

In the drawings,

FIG. 18 is a schematic view of an electric toothbrush having an electromagnetically encoded brush attachment with a transponder bonded thereto by adhesion or integrated therein and a corresponding detection device in the handle section according to a further preferred embodiment of the invention;

FIG. 18A shows a possible arrangement of a transponder.

Figure 2:
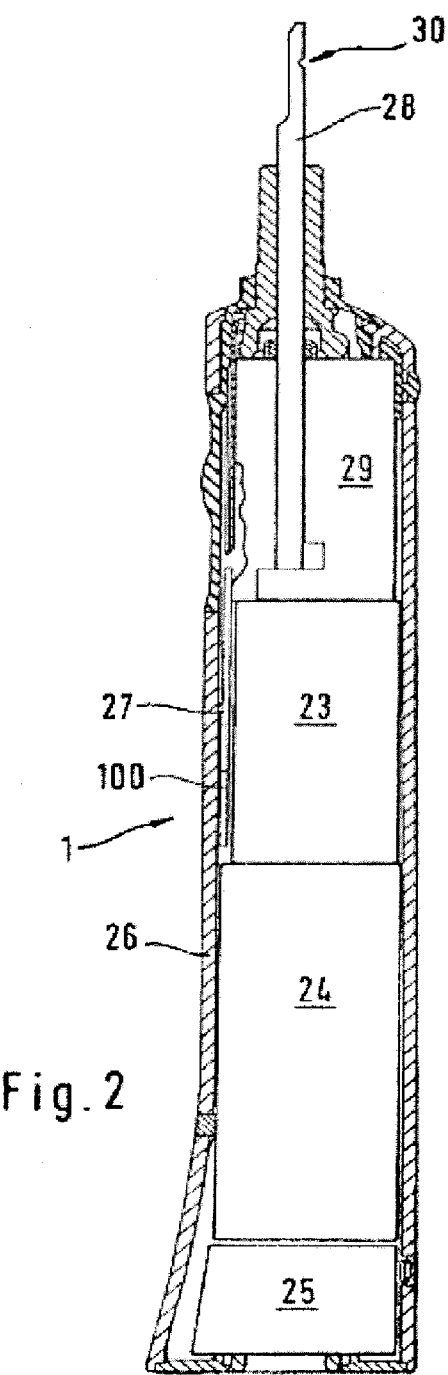
FIG. 2 is a schematic longitudinal sectional view of the handle section of the electric toothbrush of FIG. 1, showing arranged in the housing thereof the drive motor with gearing and drive shaft, the storage battery for the drive motor and the charging module for the storage battery.

The electric toothbrush shown in the Figures has a handle section 1 with a closed housing 26 accommodating, among other components and as illustrated in FIG. 2, in a manner known in the art an electric motor 23, a storage battery 24 adapted to be coupled to a charging station through a charging module 25 disposed at the bottom, and a control device 27 which may possess a printed circuit board or microprocessor. Various brush attachments 2 are seatable upon the end of the handle section 1 to function as brushing or cleaning tools. By means of a coupling device 3 the brush attachment 2 can be mechanically coupled to the handle section 1 in order to transmit the driving motion of the electric motor to the brush head 4 of the brush attachment 2. The coupling device 3 which may be made of one or several parts or pieces comprises a positive- or frictional-engagement element for positioning the cleaning tool body in its proper location and, in addition, a drive coupling which transmits the driving motion of the drive to the brush head 4 of the brush attachment. Protruding from the end of the handle section 1 is a drive shaft 28 adapted to be driven by the drive motor 23 via a gearing 29 in a manner equally known in the art. The drive shaft 28 has a coupling section 30 adapted to receive by positive or frictional engagement therewith a complementary coupling section of a drive shaft arranged in the cleaning tool 2, so that the driving motion is transmitted, enabling the brush head 4 of the brush attachment to be driven in a reciprocating, rotating, oscillating, etc. manner.

The control device 27 has an electronic interlock device 100 which prevents operation of the drive of the handle section unless a compatible brush attachment 2 is attached to the handle section 1 which then releases the drive for operation. The key to this electronic interlock device 100 is an encoding or interlock canceling element 7 provided on the brush attachment 2.

To identify the brush attachment 2 when attached, provision is made on the handle section 1 for an encoding detection device 5 or a device for detecting the presence of the interlock canceling element 7. In response to a signal from this device or encoding detection device 5, the control device 27 releases the drive for operation or not.

Figure 3:
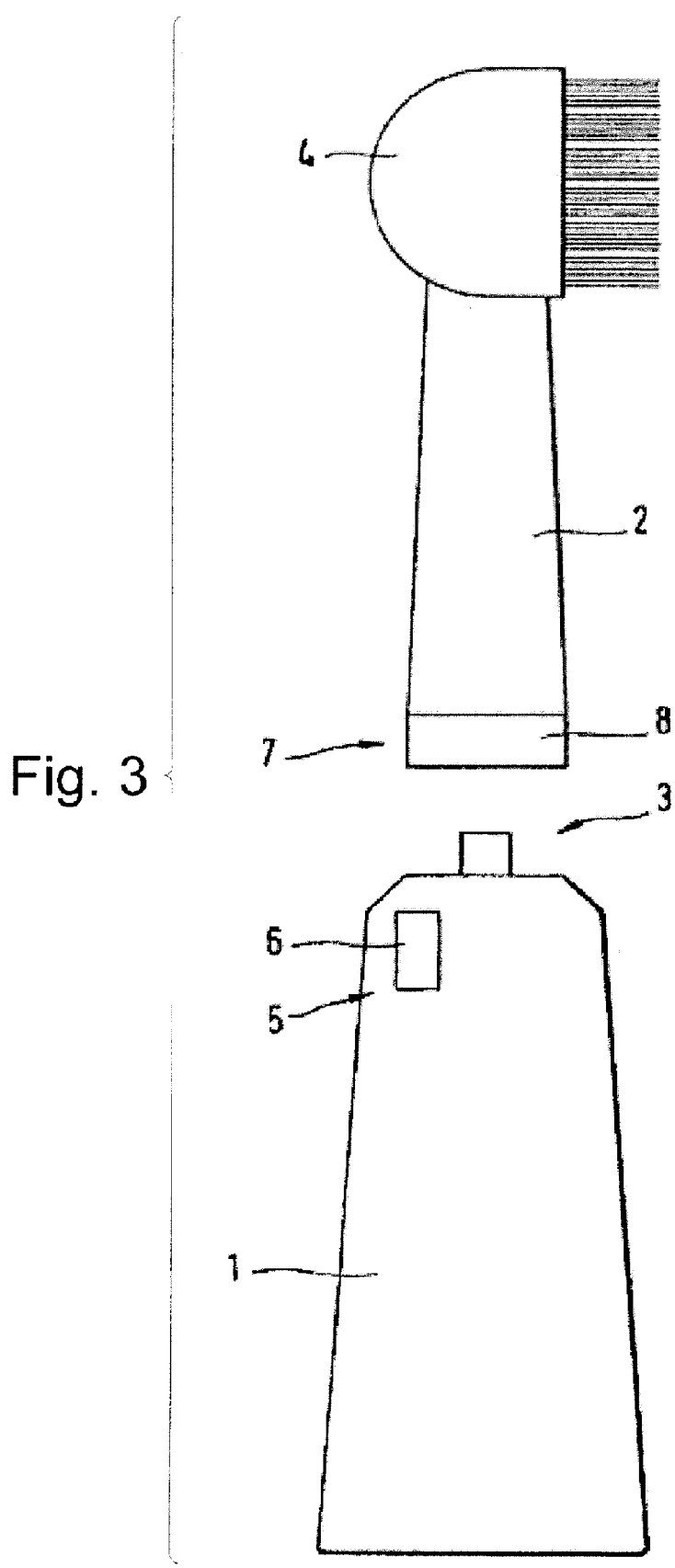
FIG. 3 is a schematic view of an electric toothbrush, showing a magnetic encoding of the brush attachment and a Hall sensor for detecting the encoding according to a preferred embodiment of the invention.
Figure 4:
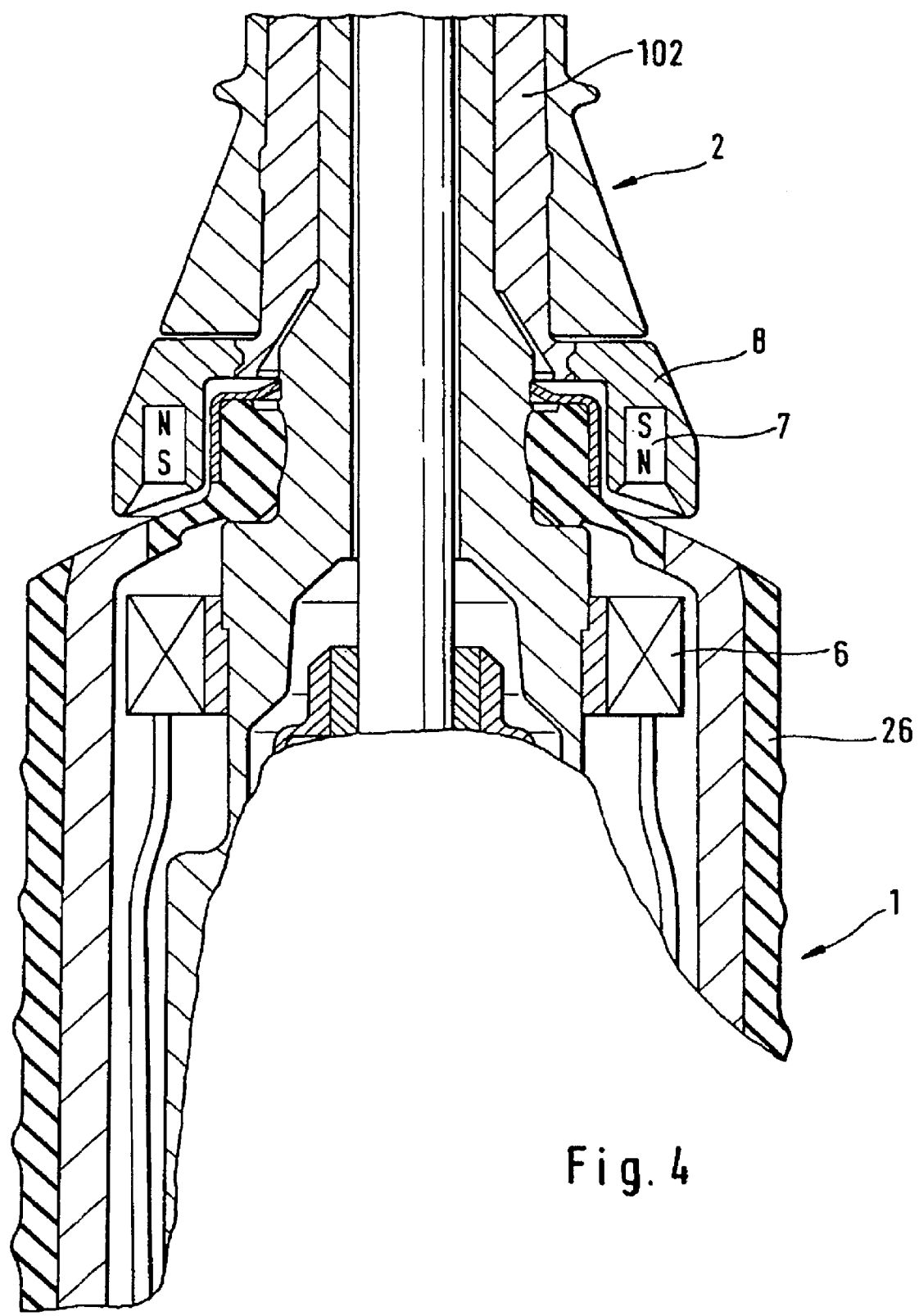
FIG. 4 is a sectional detail view of the toothbrush of FIG. 3, showing the arrangement of the Hall sensor and the magnetic encoding of the brush attachment which is coupled to the handle section.

According to FIG. 3 a Hall sensor 6 is provided at the coupling end of the handle section 1 in order to read, meaning identify, a magnetic encoding 7 on the brush attachment 2. The magnetic encoding 7 is formed by a slip-on ring 8 or a profiled ring 102 as disclosed in WO 99/20202, which is provided at the coupling end of the brush attachment 2. The slip-on ring 8 is available in a variety of colors containing either permanent magnets or like magnetic bodies or, depending on the color, a different number of magnetic particles or magnetic bodies differing in number, magnetic orientation and/or magnetic field strength. As FIG. 4 shows, the slip-on ring 8 or profiled ring 102 may be positioned in its proper location on the body of the brush attachment advantageously by positive engagement therewith, being in particular snap-fitted thereto. This connection may be constructed such that the ring 8 or profiled ring 102 is securable to the body of the brush attachment in only one predetermined orientation relative thereto. The Hall sensor 6 in the handle section 1 supplies a signal correlating with the magnetic body or the number of magnetic particles or the arrangement of the magnetic bodies, the value of this signal being characteristic particularly of the respective brush attachment 2 and suitable for further processing by the control device in the handle section 1. The color of the slip-on ring 8 makes it easy to remember which brush attachment 2 is assigned to which user.

As FIG. 4 shows, the magnetic encoding 7 and the Hall sensor 6 are disposed at the coupling ends of the brush attachment and the handle section, respectively, lying advantageously opposite each other in order to enable an accurate detection to be accomplished.

Figure 1:
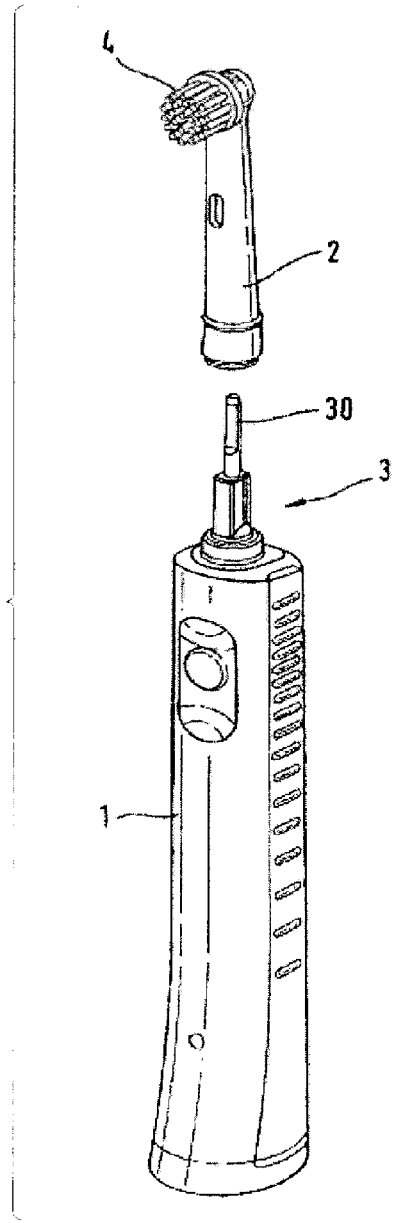
FIG. 1 is a perspective view of an electric toothbrush having a handle section and a brush attachment attachable thereto.

The electric toothbrushes according to the further embodiments illustrated in the further Figures are constructed basically in the same way as the toothbrush illustrated in FIGS. 1 and 2, so that like components are assigned like reference numerals, and the subsequent description deals only with the different implementations of the encoding 7 of the brush attachments 2 and the corresponding encoding detection devices 5 on the handle section 1.

Figure 5:
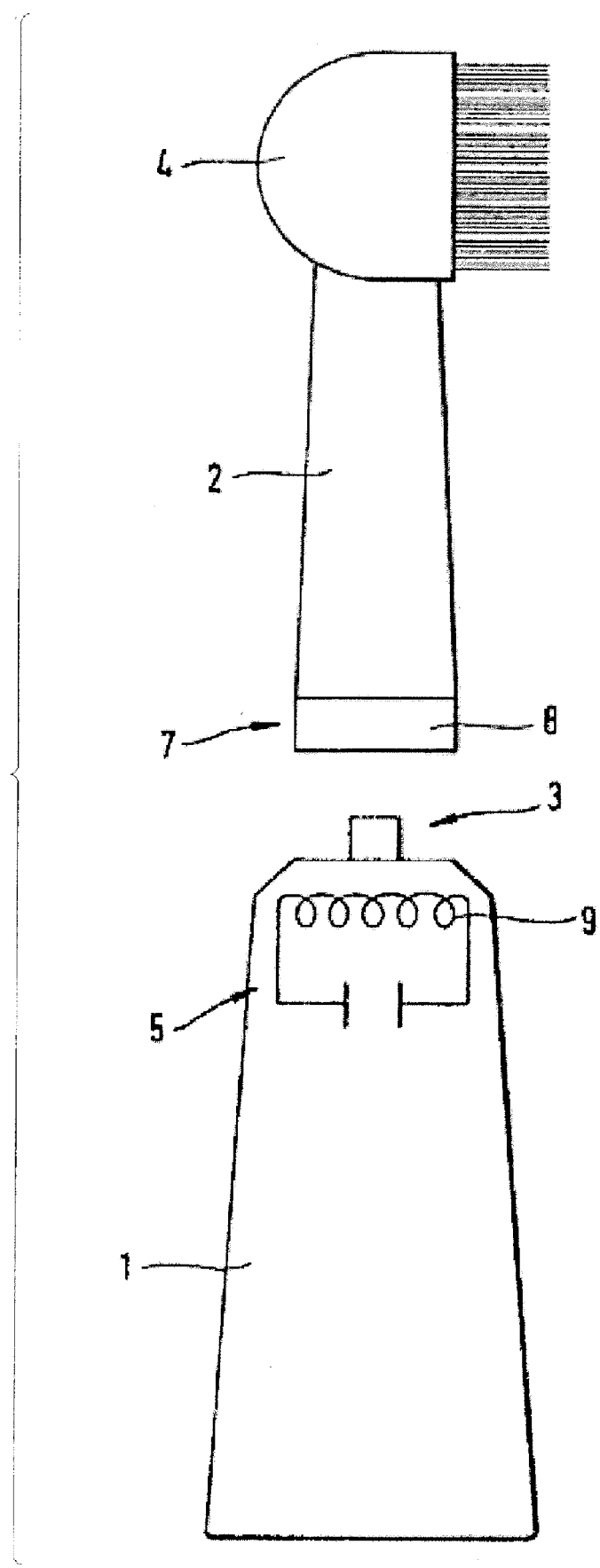
FIG. 5 is a schematic view of an electric toothbrush having a magnetically encoded brush attachment and an LC oscillator in the handle section to detect the encoding according to a further preferred embodiment of the invention.
Figure 6:
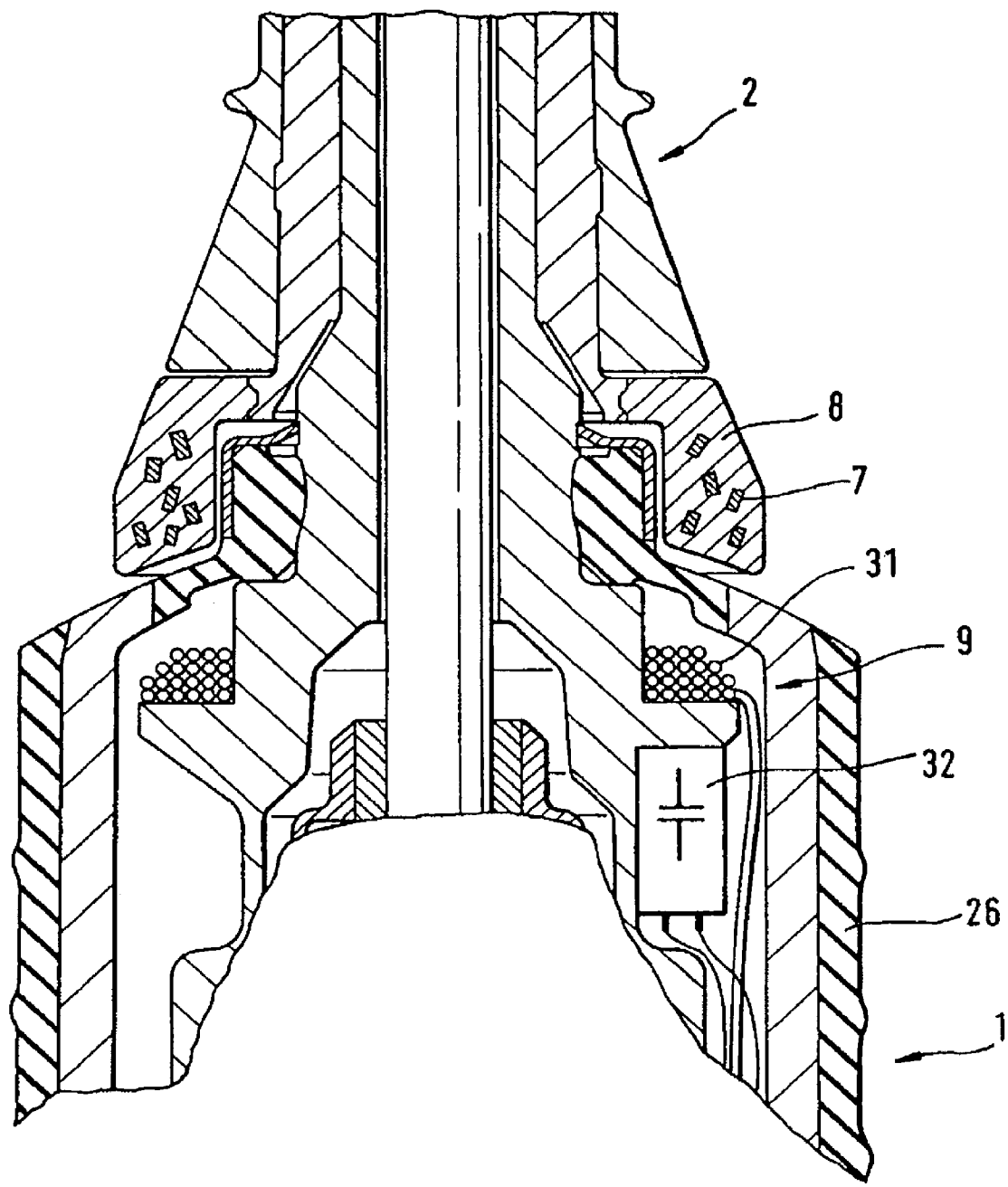
FIG. 6 is a sectional detail view of the toothbrush of FIG. 5, showing the arrangement of the LC oscillator and the magnetic encoding of the brush attachment which is coupled to the handle section.

In the electric toothbrush illustrated in FIGS. 5 and 6 the brush attachment 2 carries likewise a slip-on ring 8 which is available in various colors and contains magnetic particles differing in number depending on the color. To detect the magnetic encoding of the brush attachment 2, the recognition device 5 has an LC oscillator 9 which is disposed at the coupling end of the handle section 1 and detuned by the magnetic material in the brush attachment 2, thereby supplying different frequencies assignable to the brush attachments. The corresponding frequency signals are further processed by the control device in the handle section 1 in order to effect deactivation of the interlock device 100 or also to set further operating parameters or to process and indicate user-specific data.

As FIG. 6 shows, the LC oscillator has a coil 31 and a capacitor 32 which are both disposed in the coupling end region of the handle section. The coil is arranged directly at the end. It may be mounted on a shoulder or the like of a handle section chassis. The capacitor is positioned underneath the coil which faces the encoding ring 8. This enables the encoding to be detected with precise accuracy.

Figure 7:
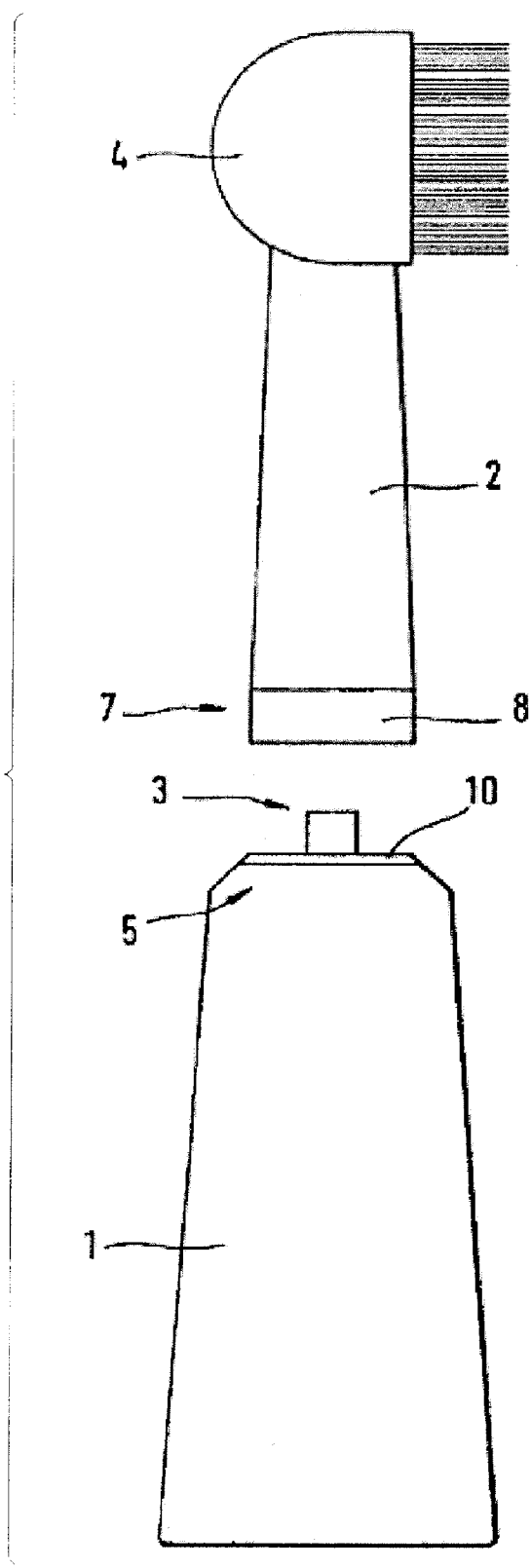
FIG. 7 is a schematic view of an electric toothbrush having a magnetically encoded brush attachment and a handle section with reed contacts to detect the encoding according to a further preferred embodiment of the invention.
Figure 7A:
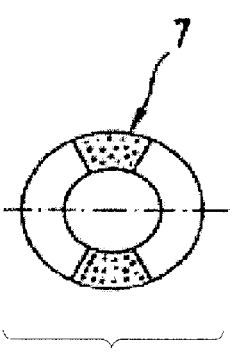
FIG. 7A shows a possible arrangement of magnetic material.
Figure 8:
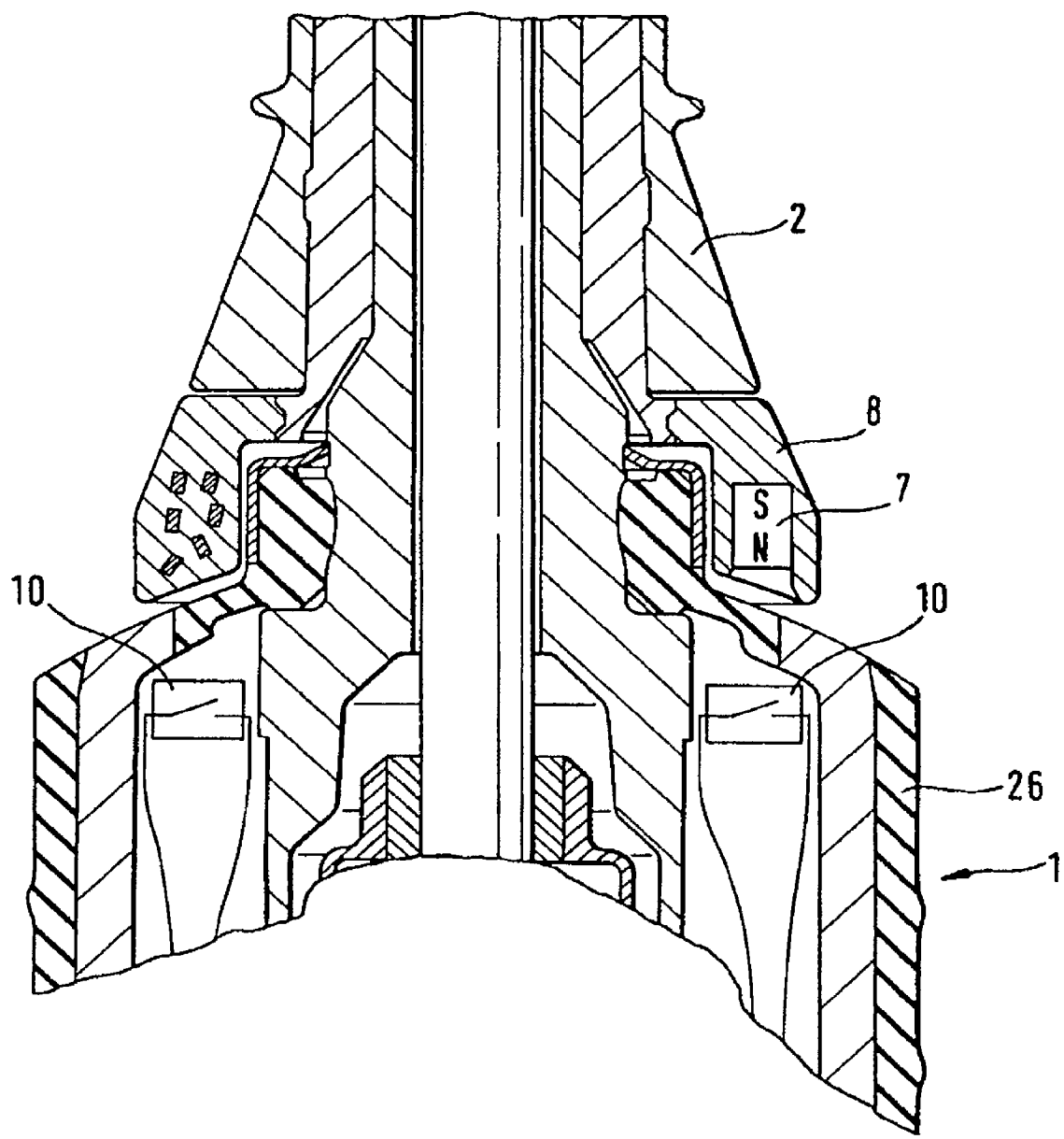
FIG. 8 is a sectional detail view of the toothbrush of FIG. 7, showing the arrangement of the reed contacts and the magnetic encoding of the brush attachment which is coupled to the handle section.

FIGS. 7 and 8 show a further embodiment of an electric toothbrush in which the slip-on ring 8 of the brush attachment 2 is provided with magnetic material only at defined locations on its circumference (cf. FIG. 7a). The recognition device 5 comprises reed contacts 10 (cf. FIG. 8) arranged in the handle section 1 at the handle end close to the coupling device 3. When the brush attachment 2 is seated down onto the handle section 1, defined actuation of the reed contacts 10 takes place in accordance with the magnetic encoding of the slip-on ring 8. Depending on the combination of contacts actuated, a specific brush attachment can be identified. Here too, the slip-on ring 8 is a colored ring to make it easier for the user to identify his or her assigned brush. For enhanced response of the reed contacts, the magnetic ring 8 or profiled ring 102 and the reed contacts 10 have their respective ends in relative opposite arrangement.

FIGS. 9 to 12 illustrate a preferred and advantageous embodiment of an electric toothbrush in which the brush attachment 2 is detected optically. The recognition device 5 comprises in the handle section 1 one or several optical waveguides 11 exiting at the coupling end of the handle section and experiencing defined interruptions or partial obstructions by the brush attachment 2. The brush attachment 2 returns the light signal emitted from the optical waveguide 11 to the handle section 1 in encoded form, the encoded light signal being directed through the optical waveguide 12 to a sensor 13 which detects whether or not and/or in which intensity light was returned and issues a corresponding recognition signal enabling the brush attachment to be identified and/or the interlock device 100 to be actuated. For encoding and returning the light signal the brush attachment 2 may possess a preferably likewise colored slip-on ring 8 in which corresponding optical waveguides 14 are provided (cf. FIG. 9a). According to a further variant the light emitted from the handle section 1 through the optical waveguide 11 is reflected individually by the brush attachment 2 or a correspondingly encoded slip-on ring 8. Depending on the intensity of reflection a particular brush attachment can be identified.

Figures 9, 9A:
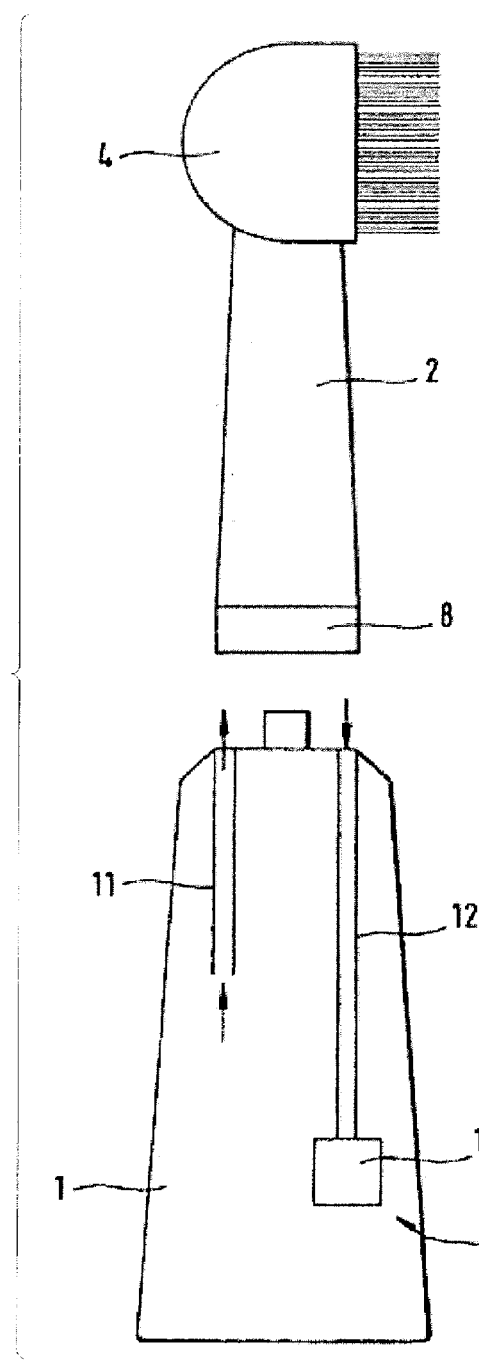
FIG. 9 is a schematic view of an electric toothbrush having an optically encoded brush attachment and a handle section with optical waveguides according to a further preferred embodiment of the invention.
FIG. 9A shows a possible arrangement of optical waveguides.
Figure 10:
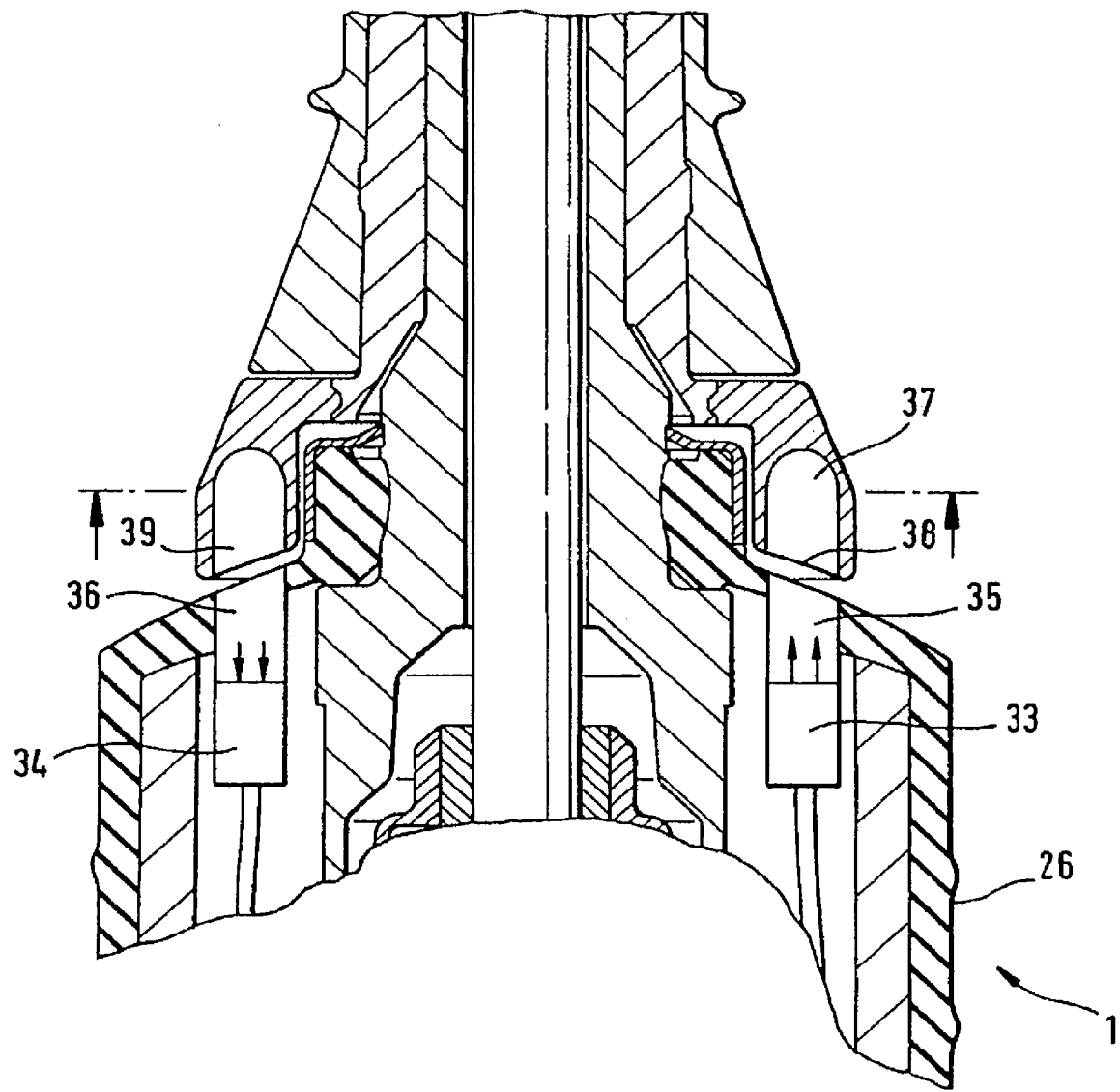
FIG. 10 is a sectional detail view of a toothbrush similar to FIG. 9, showing the arrangement of a light emitter and a light detector in the handle section and an encoding of the brush attachment in the form of an optical waveguide, with the brush attachment and the handle section being shown in coupled condition.
Figure 11:
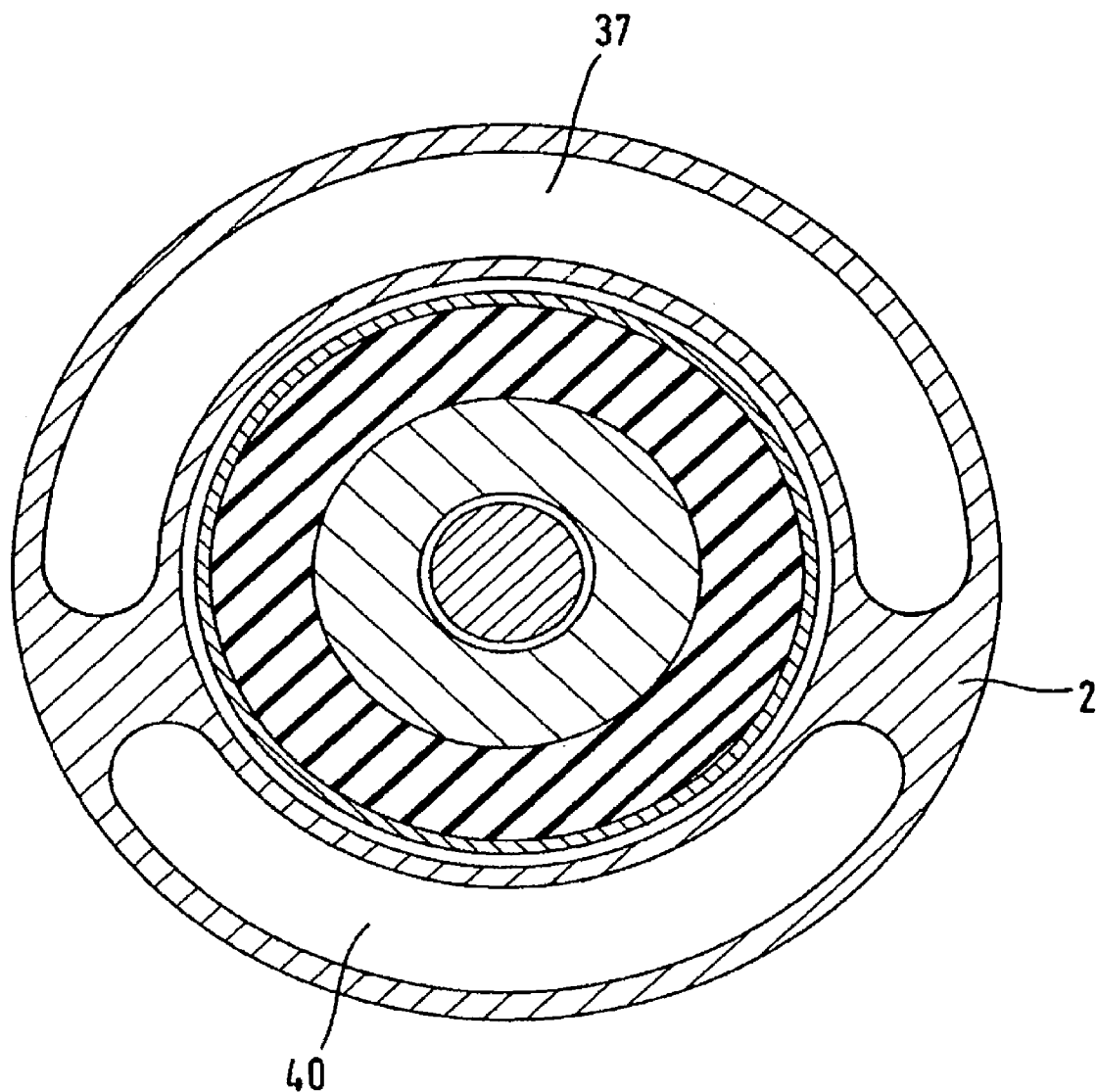
FIG. 11 is a top plan view of the optical waveguides at the end, close to the handle section, of the brush attachment of FIG. 10.

FIGS. 10 and 11 illustrate an advantageous variant of the toothbrush of FIG. 9 with optical encoding of the brush attachment and corresponding detection of the encoding by the handle section 1. Provided in the handle section 1 directly at its coupling end are a light emitter 33 and in circumferentially offset position a light detector 34 which, through a light exit opening 35 and a light entrance opening 36 provided at the end of the handle housing 26, look at the coupled brush attachment 2. The light exit and light entrance openings may be closed by a transparent material to obtain a closed construction of the housing 26. Both the emitter 33 and the detector 34 are connected to the control and evaluation device 27 of the handle section 1. As FIG. 11 shows, the slip-on ring 8 of the brush attachment 2 accommodates an optical waveguide 37 receiving the light emitted by the emitter 33 through a light entrance opening 38 (cf. FIG. 10), encoding and returning it through a light exit opening 39 in the slip-on ring 8 to the detector 34 in the handle section. The light may be guided in a variety of ways, particularly by reflection. In this case the optical waveguide may be configured as a reflector. The signal issued by the light detector can be evaluated by the control device of the handle section 1 to identify the specific brush attachment attached. The optical waveguide 37 extends in the slip-on ring 8 in an approximately arcuate configuration (cf. FIG. 11). To increase the possibilities of encoding, multiple light processing devices may be provided. FIG. 11 shows a second optical waveguide 40. Encoding may be performed by selection of a particular one of multiple light detectors to which the respective optical waveguide returns the received light. Encoding may also be performed by the optical waveguides modifying or processing the received light in different ways, in particular reflecting it in different intensities. This is then converted into a corresponding signal by the light detector.

Figure 12:
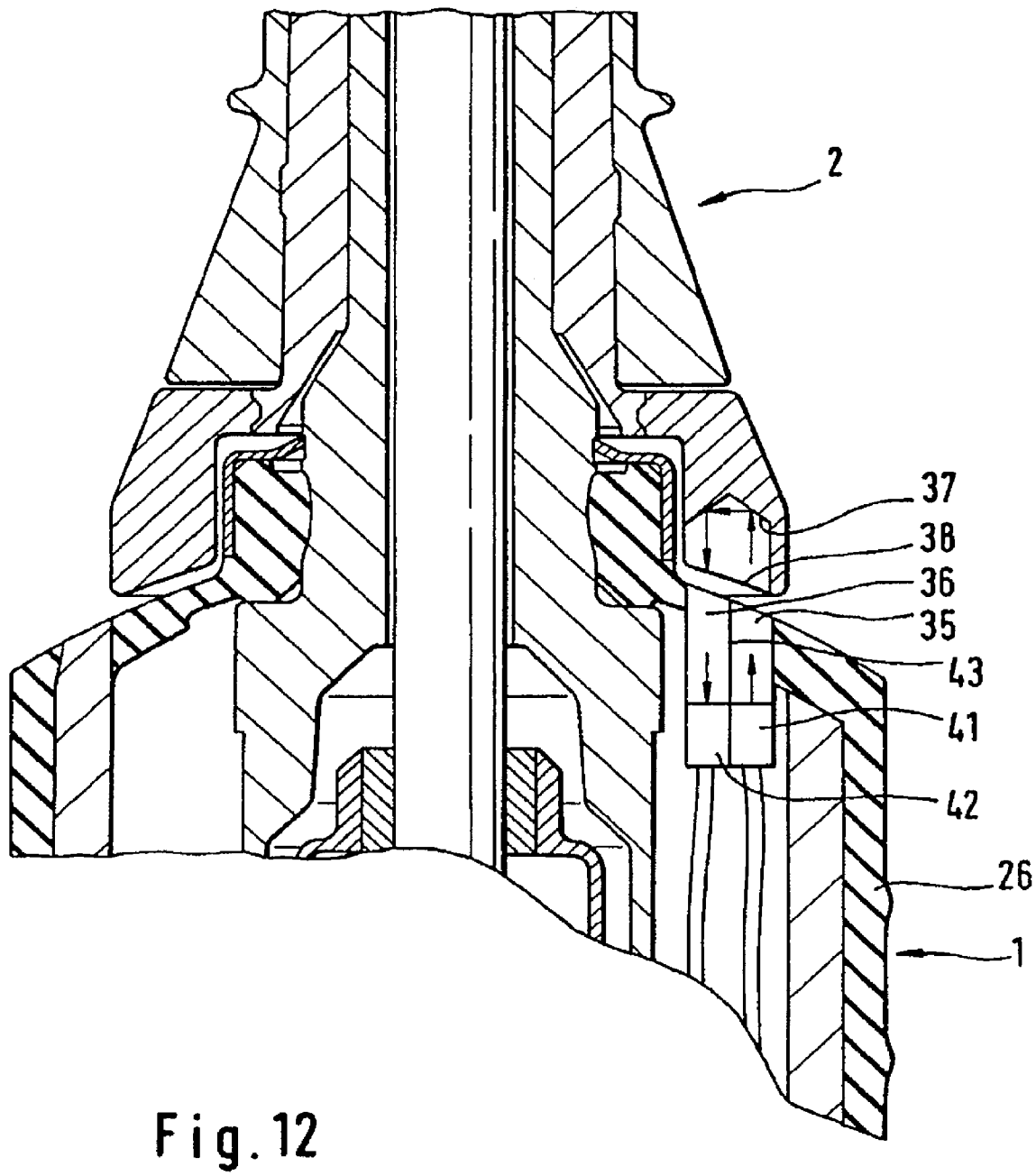
FIG. 12 is a sectional detail view of a toothbrush similar to FIG. 10, showing the arrangement of a light emitter and a light detector in the form of a single integrated component in the handle section and an encoding of the brush attachment in the form of an optical waveguide, with the brush attachment and the handle section being shown in coupled condition.

FIG. 12 shows a further variant of optical encoding. The light emitter 41 and the light detector 42 are constructed as an integral component. A partition wall 43 is preferably provided to separate the light entrance and light exit openings from each other. The light may be encoded in particular by different magnitudes of reflection.

Figure 13:
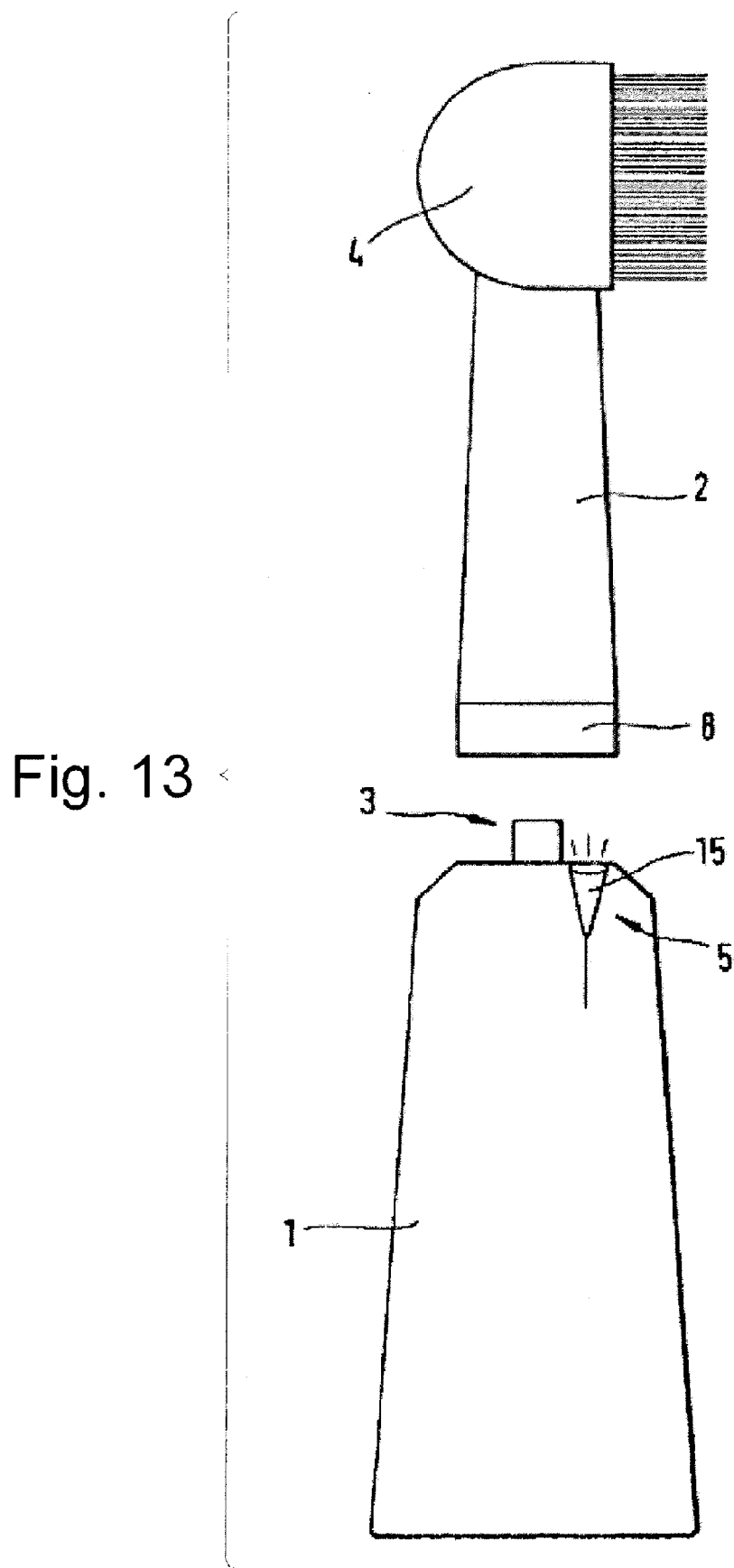
FIG. 13 is a schematic view of an electric toothbrush having an optically encoded brush attachment and a handle section with color sensor for identification of the encoding of the brush attachment according to a further preferred embodiment of the invention.
Figure 14:
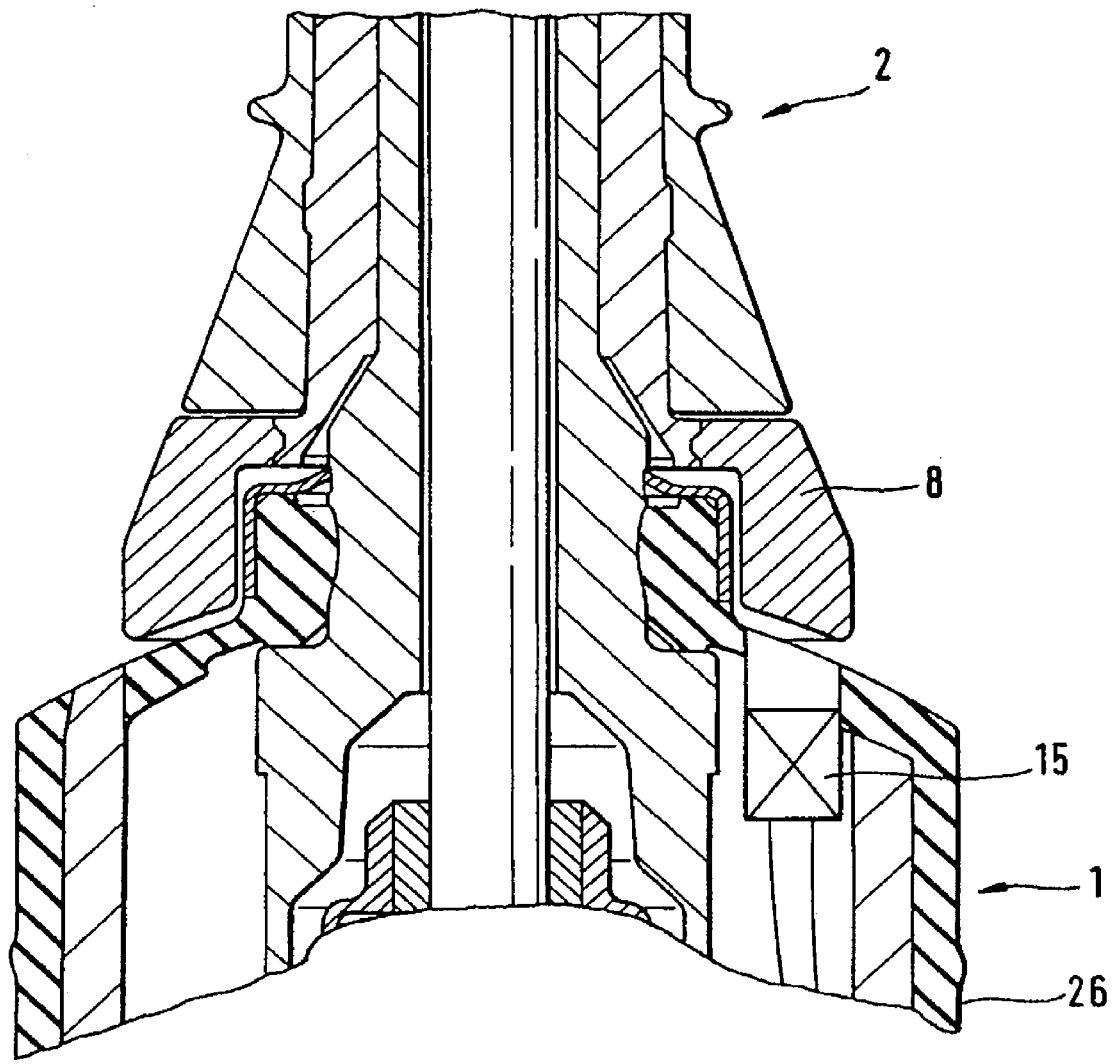
FIG. 14 is a sectional detail view of the toothbrush of FIG. 13, showing the arrangement of the color sensor in the handle section and the color code of the brush attachment which is coupled to the handle section.

The embodiment of an electric toothbrush illustrated in FIGS. 13 and 14 has similar to the preceding embodiments a colored slip-on ring 8 secured to the end of the brush attachment 2 close to the coupling device 3. The handle section 1 has as recognition device 5 a color sensor 15 disposed at the coupling end of the handle section 1 and oriented in the direction of the colored slip-on ring 8. The color sensor 15 detects the color of the slip-on ring 8, enabling the brush attachment or the user of the toothbrush to be determined. Conveniently, the color sensor is arranged directly at the coupling end of the handle section 1 and oriented in the direction of the ring 8 when the brush attachment sits on the handle section 1.

Figure 15:
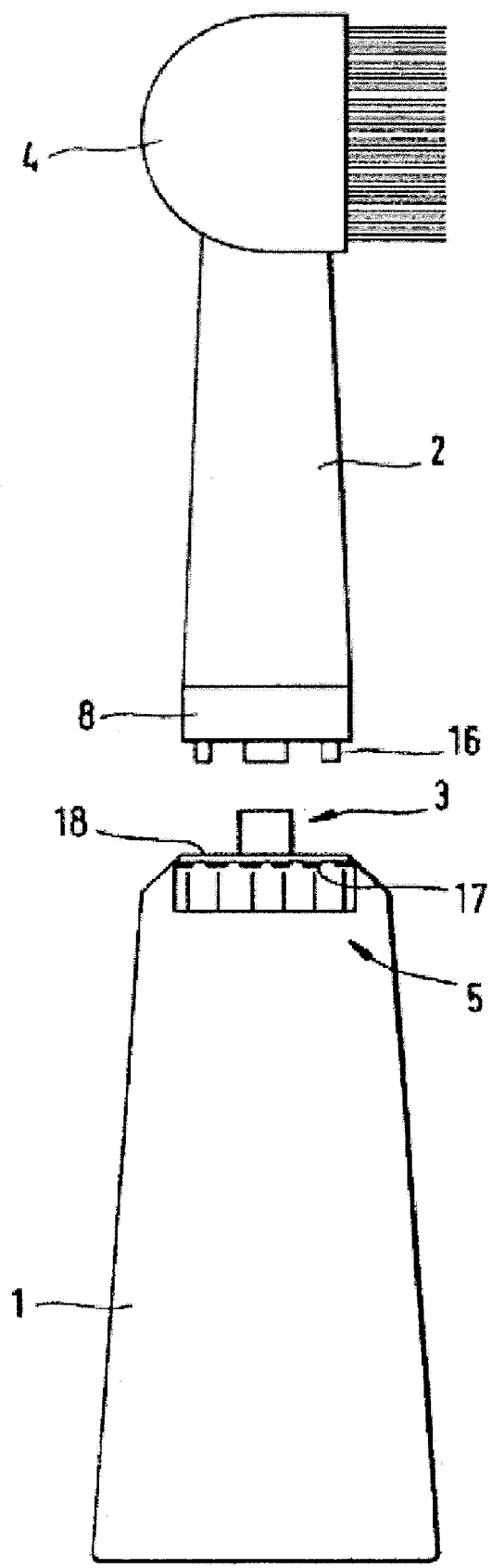
FIG. 15 is a schematic view of an electric toothbrush having a brush attachment encoded mechanically by its shape in accordance with another preferred embodiment of the invention.
Figure 16:
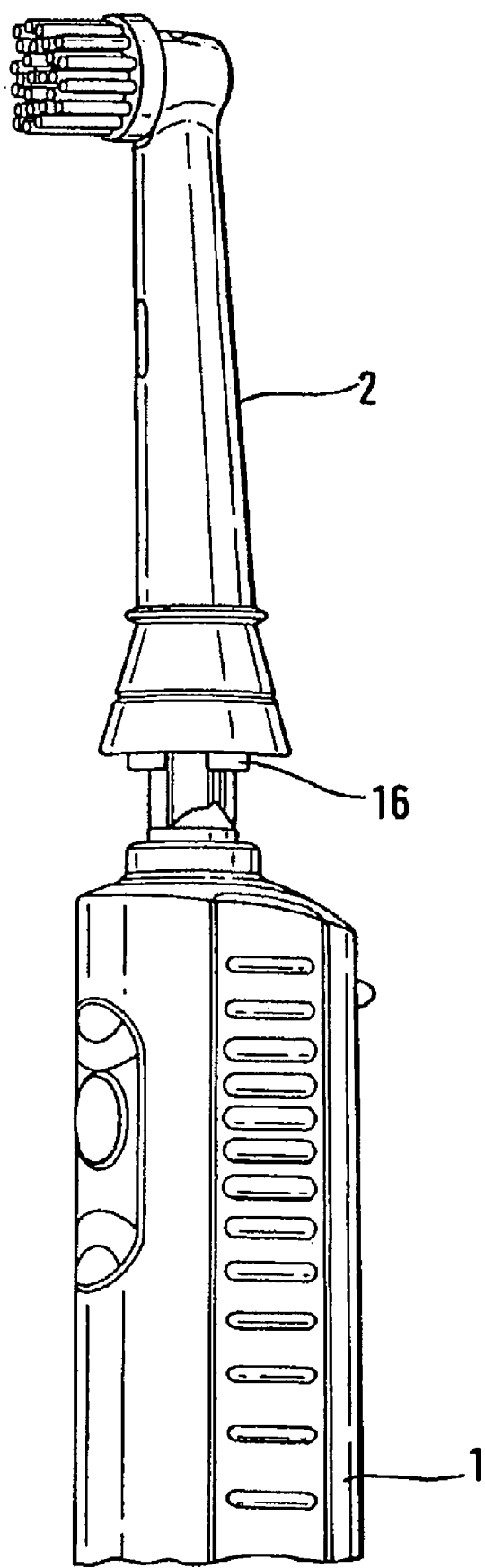
FIG. 16 is a perspective view of the toothbrush of FIG. 15, showing the brush attachment as it is being coupled to the handle section.
Figure 17:
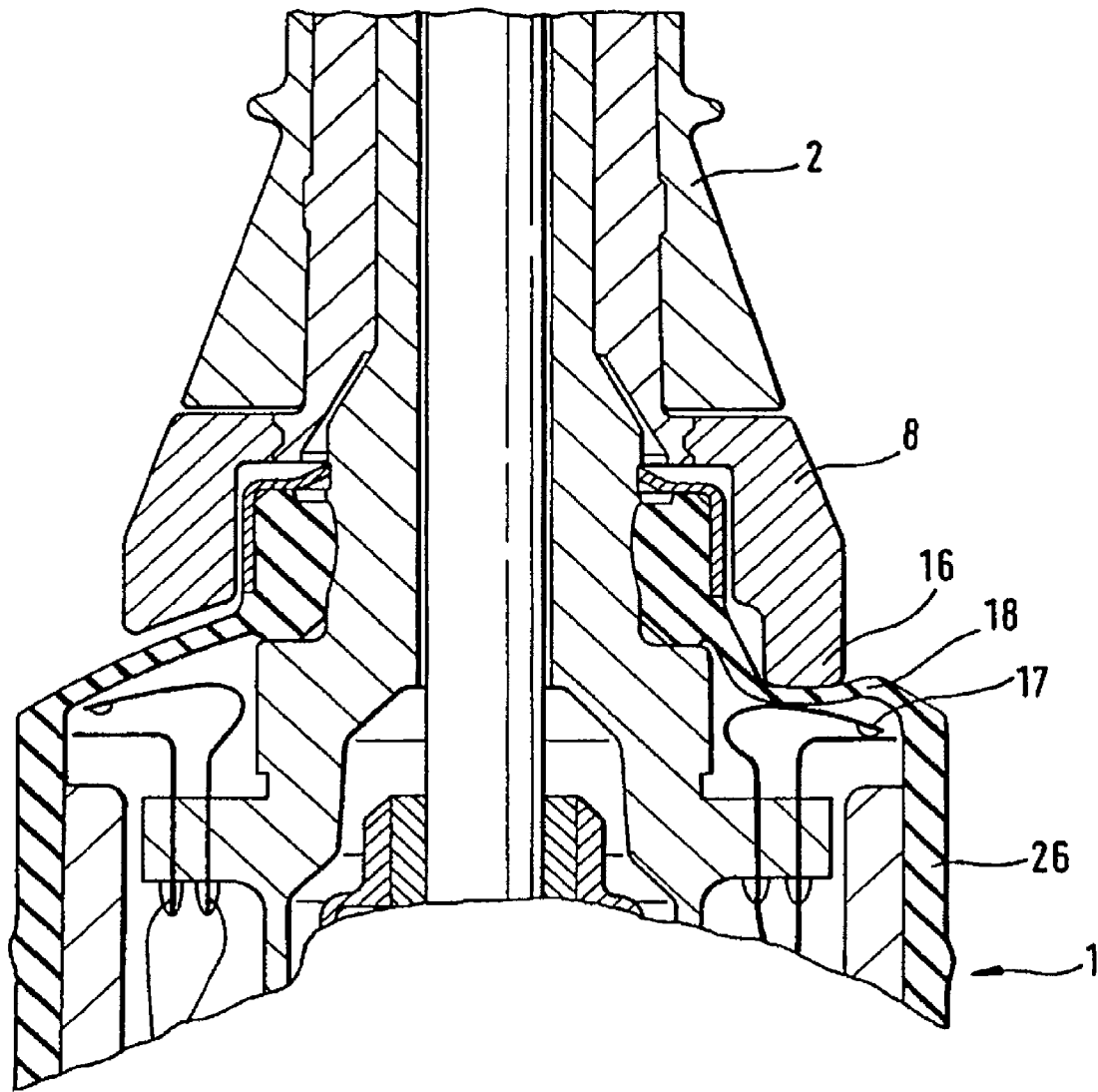
FIG. 17 is a sectional detail view of the toothbrush of FIGS. 15 and 16, showing the arrangement of the encoding projections on the brush attachment and the sensing elements in the form of electromechanical contacts for sensing the encoding projections, with the brush attachment and the handle section being shown in coupled condition.

FIGS. 15, 16 and 17 illustrate an embodiment of an electric toothbrush in which the brush attachments 2 are recognized mechanically. The colored slip-on ring 8 at the end of the brush attachment 2 is an individually shaped encoding body having preferably projections 16 or recesses in the form of ribs or grooves. According to one embodiment of the invention the shaped bodies extend as projections from the end of the brush attachment, in particular essentially parallel to the longitudinal axis of the brush attachment. At the opposite end of the handle section 1 provision is made for elastically deformable sensing elements in the form of mechanical contacts 17 which are subjected to individual and defined actuation by the brush attachment 2, meaning the projections 16 on the slip-on ring 8, so that the respective brush attachment 2 is identified according to the combination of actuated contacts. The shaped encoding bodies 16 have for this purpose actuating or pressure application surfaces which are arranged, oriented and/or configured such as to depress the sensing element a predetermined amount when the brush attachment is seated down on the handle section. The sensing elements generate a signal responsive to the amount of depression, in the simplest case an on-off signal according to the contacting of the contact sections provided at the sensing elements' ends. Actuation of the mechanical contacts can be checked preferably electrically. To cover the mechanical contacts 17 and shield them against the environment a soft membrane 18 may be placed over the mechanical contacts 17 at the end of the handle section 1, through which membrane the mechanical contacts 17 can be actuated by the projections 16. To accomplish this the housing 26 may be a two-component injection molded part fabricated from hard and soft plastics material.

Figure 19:
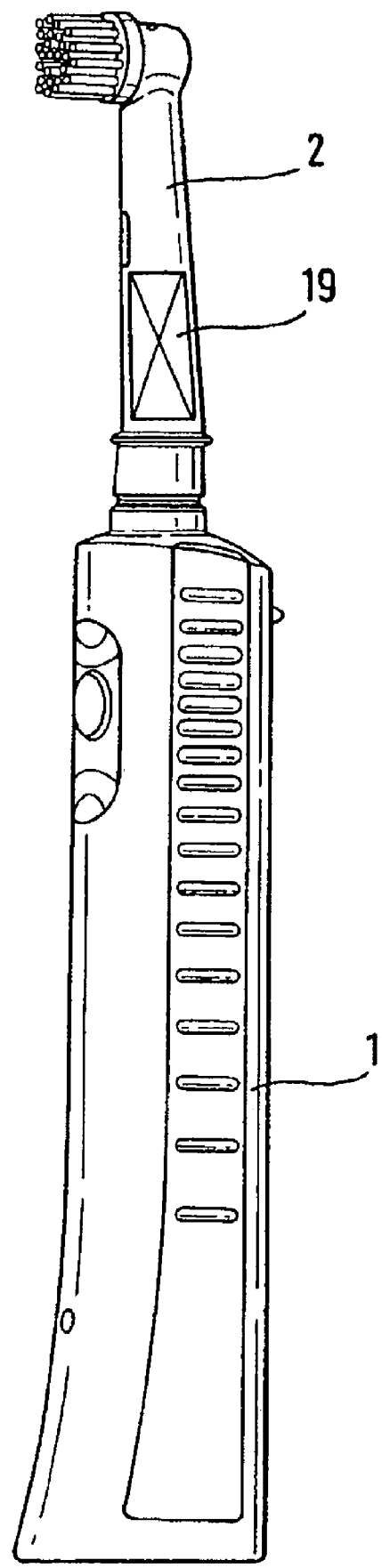
FIG. 19 is a perspective view of the toothbrush of FIG. 18.
Figure 20:
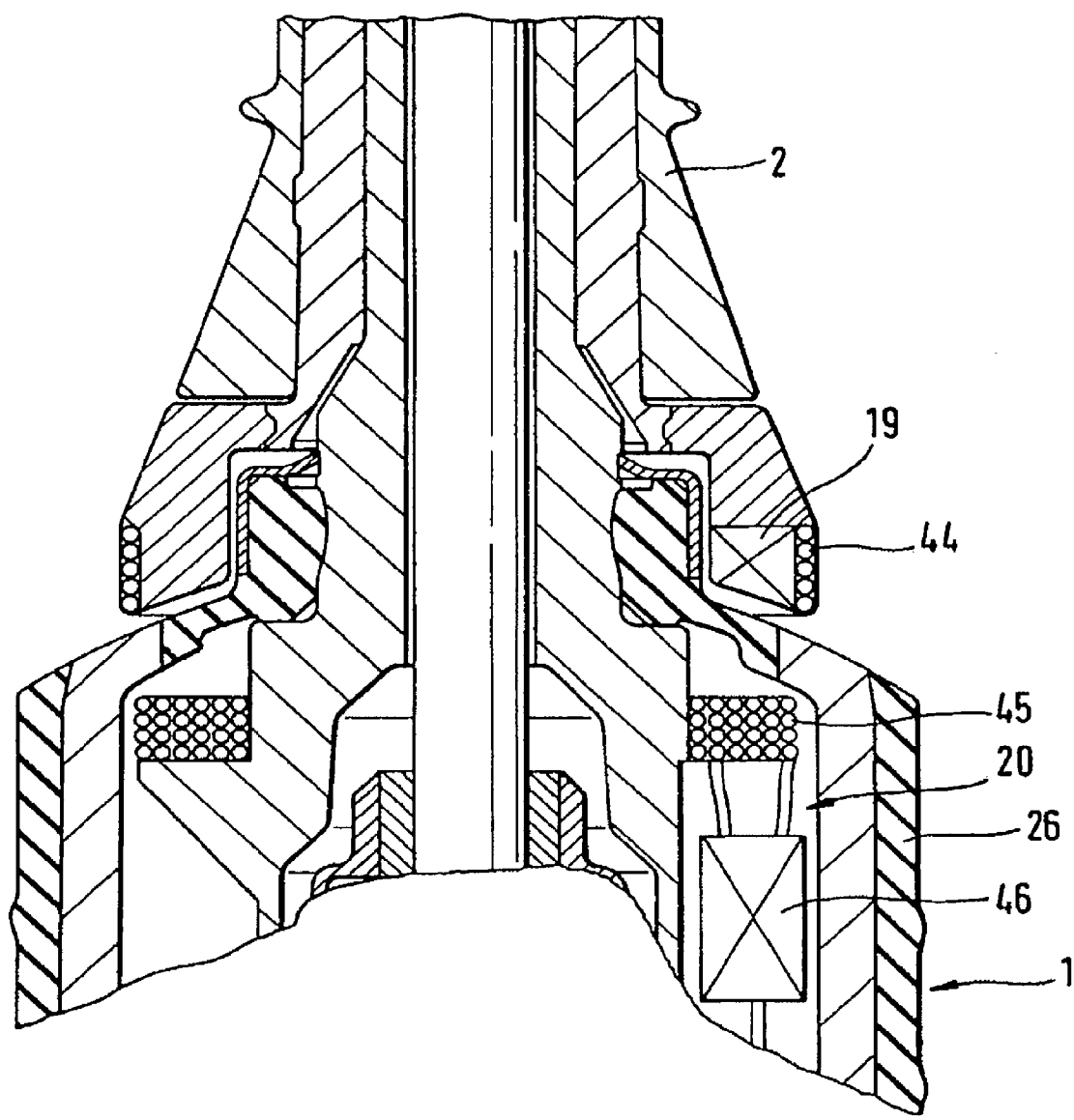
FIG. 20 is a sectional detail view of a toothbrush similar to FIGS. 18 and 19, showing the arrangement of a transponder chip in an encoding ring provided at the end of the brush attachment, and a transmitter coil and a receiver coil together with an associated electronic evaluation device in the handle section, with the brush attachment and the handle section being shown in coupled condition.

FIGS. 18 to 20 illustrate a further embodiment of an electric toothbrush in which the brush attachment 2 is detected, i.e., identified by means of radio signals. The brush attachment 2 is equipped with a transponder 19 which may be bonded by adhesion to or on the brush attachment 2 as in the form of a label referred to as smart label (FIG. 19). Advantageously, the transponder 19 may also be contained in the colored slip-on ring 8 at the end of the brush attachment (cf. FIGS. 18*a* and 20). Provided in the handle section 1 is a detector 20 tuned to the transponder 19 and serving as both a signal transmitter and a signal receiver. Via the coil 45 the detector 20 in the handle section 1 initially emits electromagnetic waves to the coil 44 connected to the transponder 19 in order to supply power to the transponder 19 or its microchip. The transponder stores the energy and sends a specific identification back to the detector 20 which receives said identification, identifies it by means of its electronic evaluation device 46 and delivers a corresponding signal to the control device 27 of the handle section 1. The coils 44 and 45 hence serve as both transmitter and receiver facility. In a preferred embodiment the coils are disposed in relative opposite arrangement at the ends of the brush attachment 2 and the handle section 1, respectively (cf. FIG. 20). The identification sent back by the transponder 19 enables the brush attachment 2 to be identified.

Figure 21:
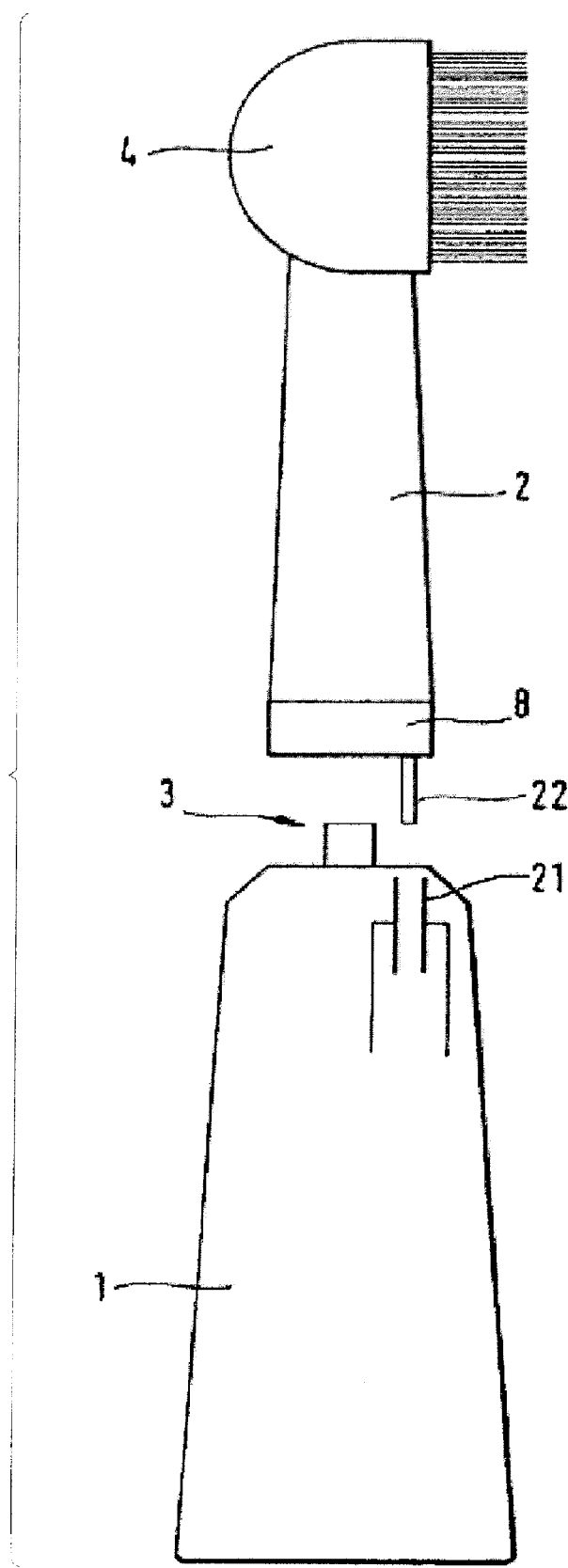
FIG. 21 is a schematic view of an electric toothbrush having a capacitively encoded brush attachment and capacitor plates in the handle section to detect the encoding of the brush attachment according to a further preferred embodiment of the invention.
Figure 22:
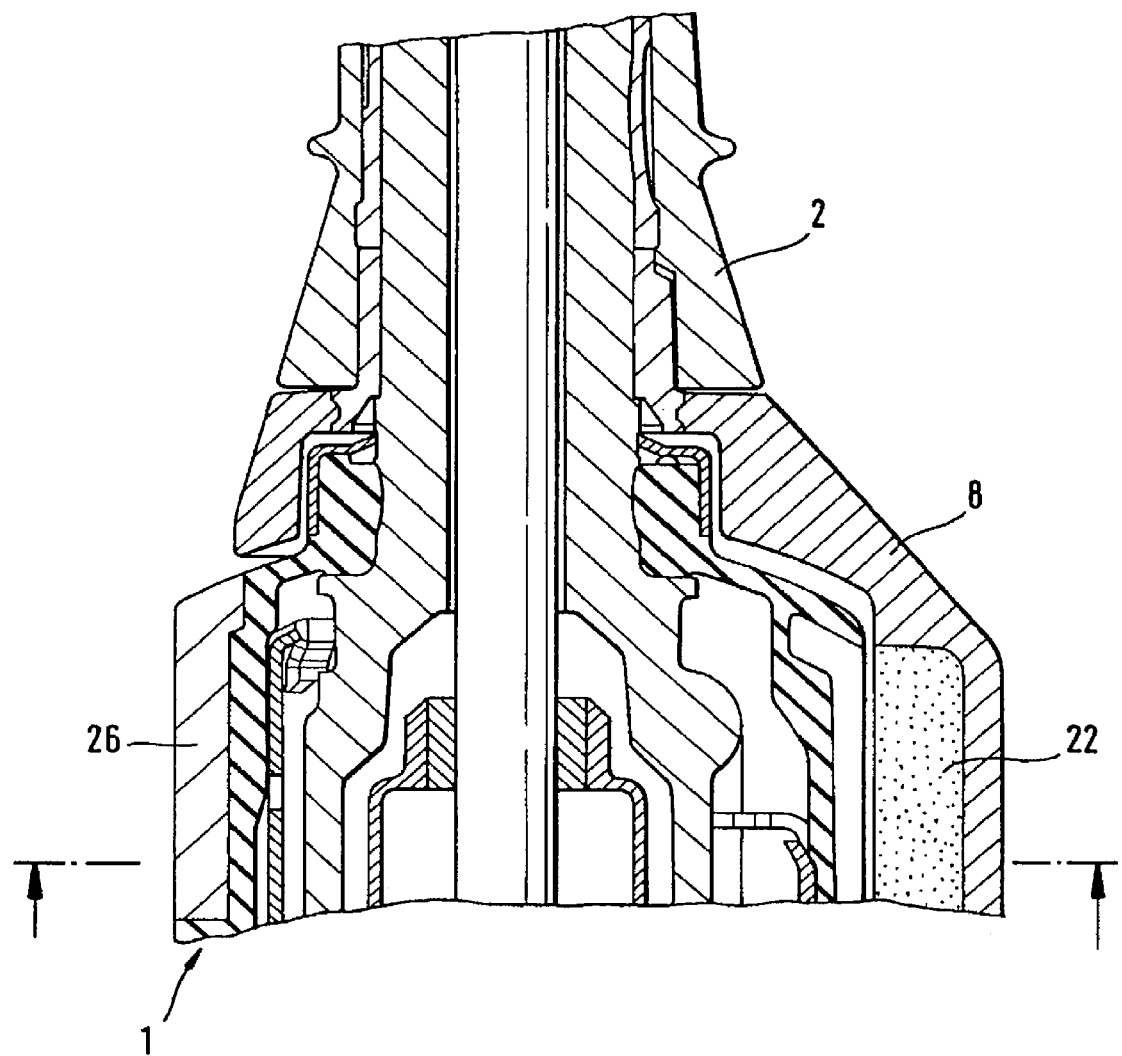
FIG. 22 is a detail view, in longitudinal section, of the toothbrush of FIG. 21, showing the arrangement of the dielectric portion of the brush attachment and the capacitor plates in the handle section, with the brush attachment and the handle section being shown in coupled condition.
Figure 23:
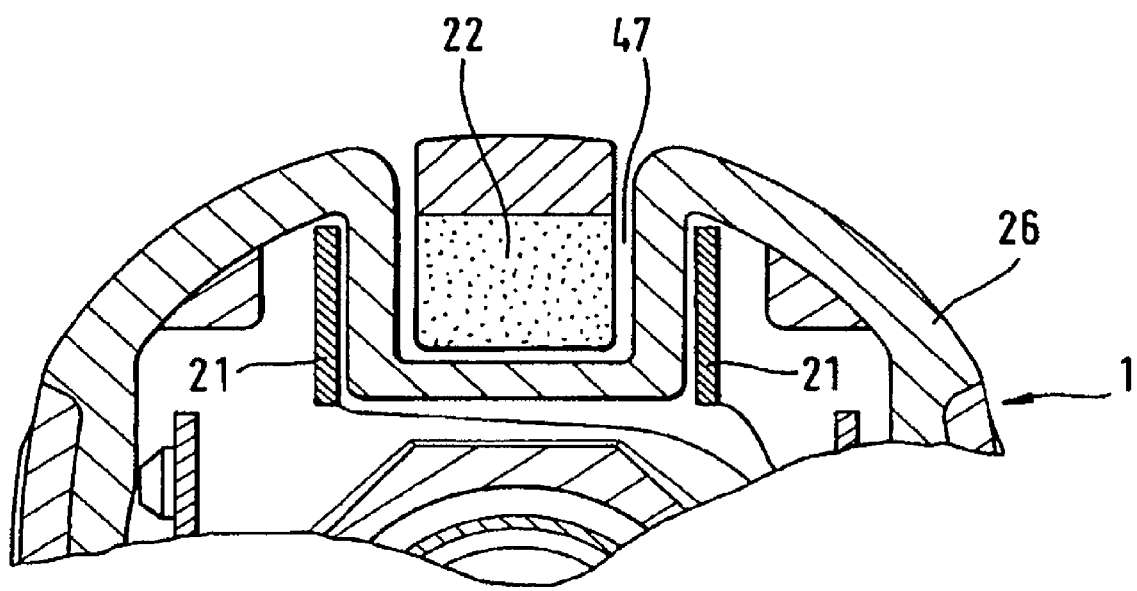
FIG. 23 is a detail view, in cross section, of the toothbrush taken along the line A-A of FIG. 22, showing the arrangement of the dielectric portion of the brush attachment and the capacitor plates in the handle section.

In the embodiment of an electric toothbrush illustrated in FIGS. 21, 22 and 23, identification of the brush attachment 2 is performed capacitively. Provided in the handle section 1 are two or several capacitor plates 21 between which a dielectric 22 is insertable to vary the capacitance of the capacitor formed by the capacitor plates 21. The dielectric 22 is arranged at the end of the brush attachment 2, and it may be in particular part of a slip-on ring 8 fittable to the brush attachment 2. The dielectric portion 22 extends preferably approximately parallel to the longitudinal axis of the brush attachment, in particular approximately parallel to its circumferential surface. Provided in the circumferential surface of the handle housing 26 is an indentation 47 open towards the end and having the form of a longitudinally parallel groove suitable for engagement by the dielectric portion 22 of the brush attachment as it is being coupled to the handle section 1. The capacitor plates 21 are disposed in the interior of the housing 26 on either side of the indentation referred to so that the dielectric comes to lie between the capacitor plates. The use of different dielectrics makes it possible to encode the brush attachments 2 individually. Depending on the capacitance or the variation in capacitance by the different dielectrics, the corresponding brush attachment 2 can be identified. In an arrangement involving several capacitors, an encoding is also obtainable by the arrangement and/or number of dielectrics. It will be understood that the capacitance of the capacitor can also be varied by a variation in the distance between the capacitor plates 21, which is accomplishable by providing the brush attachment 2 with mechanical elements acting on the capacitor.

Figure 24:
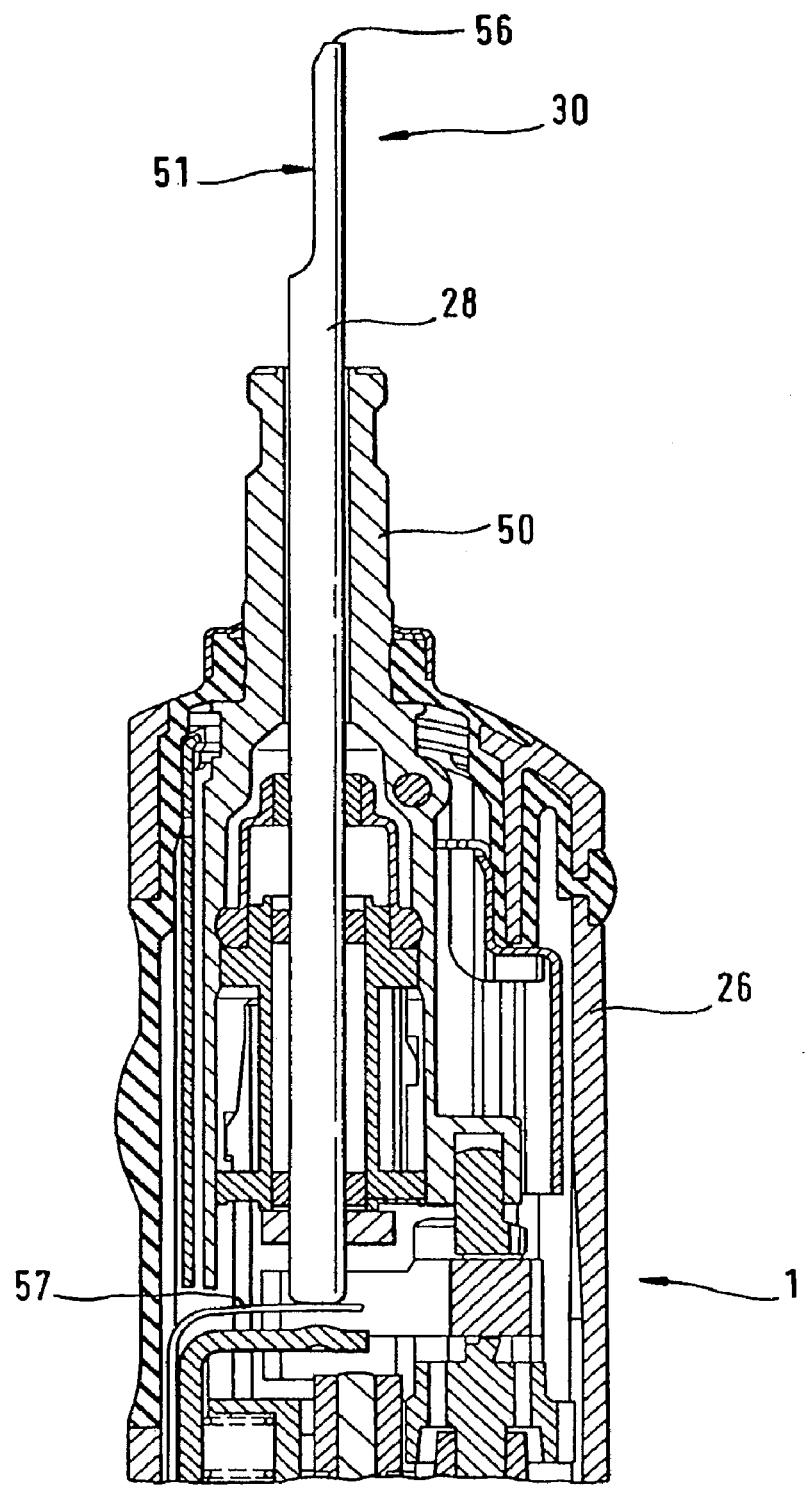
FIG. 24 is a sectional view of a handle section having a longitudinally displaceable drive shaft and an electromechanical sensing element for detecting the displacement of the drive shaft according to a further preferred embodiment of the invention.
Figure 25:
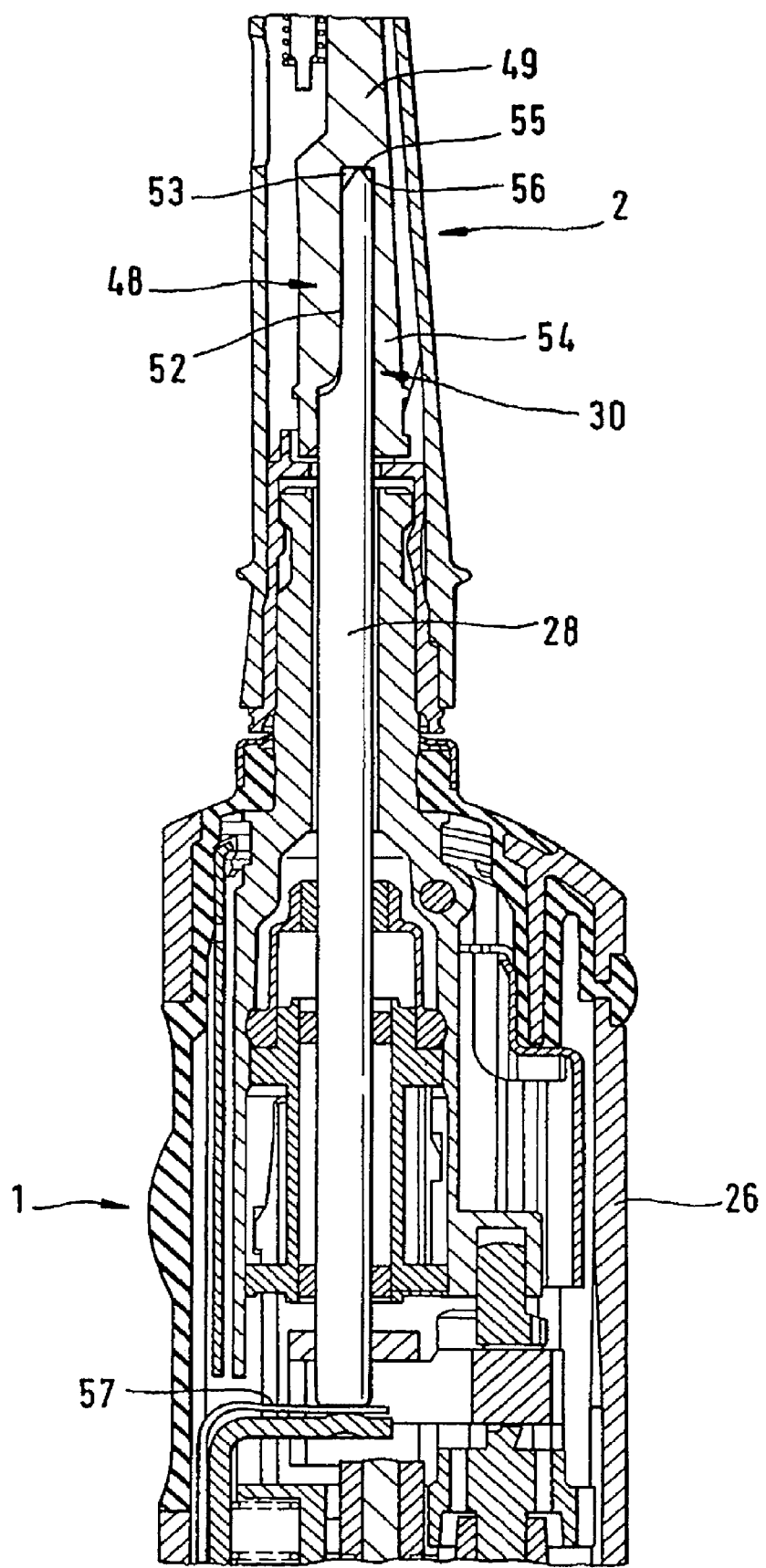
FIG. 25 is a sectional view of the handle section of FIG. 23, showing the brush attachment in coupled condition.

FIGS. 24 and 25 illustrate a specific embodiment of the invention involving a brush attachment encoded mechanically, that is, by its shape, and a mechanical detection of this encoding. The encoding of the brush attachment is part of its coupling section 48 used for coupling the drive train 49 in the brush section with the drive shaft 28 in the handle section, to be more precise, with the coupling section 30 thereof. As FIG. 25 shows, the body of the brush attachment is seated onto a brush mount 50 of the handle section 1 with an exact fit so that the brush attachment sits on the handle section 1 in a defined position. By means of detent noses and corresponding recesses the brush attachment is secured in place by making, for example, positive engagement with the handle section, that is, its brush mount. Axial securing can be accomplished also by frictional engagement. When the brush attachment is pushed onto its mount, the coupling sections 48 and 30 in the drive train also make interfitting engagement. The coupling sections are formed by a shaft stub and a complementary recess in the form of a blind-end hole in the opposite shaft end, thus enabling the shaft stub to be an exact fit within the blind-end type shaft bore. Torque transmission takes place preferably by positive engagement.

The coupling sections have complementary mating surfaces 51 and 52, preferably in the form of a flattening on the drive shaft 28 and a corresponding bore secant surface in the recess 53 of the drive shaft portion 54 of the brush attachment. A spline or a splined-shaft profile may also be provided for torque transmission.

The brush attachment, in particular the coupling section 48, has as encoding an actuating surface 55 which in coupled condition is in engagement with an associated engagement surface on the handle section 1, in particular on the coupling section 30 of the drive shaft 28. The actuating surface 55 mates with the engagement surface 56 in such manner that a predetermined interaction occurs between these two surfaces in coupled condition. In particular the actuating surface 55 is arranged and aligned so as to exert a predetermined pressure on the engagement surface 56. To be able to read or scan the configuration of the actuating surface 55, the associated engagement surface 56 is formed on a movable probe element, producing as interaction a predetermined movement of the probe element. It will be understood that it is also possible to detect a force, but a movement can be detected with greater ease. Different configurations of the actuating surfaces 56 are translated into different movements of the associated engagement surface 56 of the probe element.

As probe element the drive shaft 28 of the handle section is preferably used. The drive shaft is mounted longitudinally displaceably and preferably biased into protrusion from the handle section by means of biasing members. When the brush attachment 2 is seated down on the handle section the brush attachment's actuating surface 55 urges the drive shaft 28 a predetermined distance into the interior of the handle section 1. The displacement is detected by a displacement or motion sensor which may embody a variety of configurations, being operable for example as a light barrier. Other displacement sensors may also be employed. Preferably provision may be made for an elastically deformable sensing element with electromechanical contact of the type previously described with reference to FIG. 17. The drive shaft 28 preferably sits with a lug, preferably with its end remote from the coupling section 30, on the sensing element 57. The sensing element may at the same time serve as biasing member. When the drive shaft 28 is pressed down, the sensing element produces a corresponding signal, in particular opening or closing a corresponding contact. By suitably constructing the sensor or sensing element or multiple sensing elements the encoding of the brush attachment can be read or scanned.

As FIG. 25 shows, the actuating surface 55 is formed by the bottom surface of the blind-end type recess 53 in the brush attachment's drive shaft. The associated engagement surface is formed by the end of the drive shaft 28. While being reversible, this arrangement is preferably configured as illustrated.

Alternative embodiments of the actuating and engagement surfaces 55 and 56, respectively, are possible. In a further aspect of the invention provision may be made for conical mating surfaces. Other configurations may also be contemplated.

The invention claimed is:

1. An electric toothbrush, comprising:
a handle;
a first means that is arranged within or on the handle that emits electromagnetic wave energy when the first means is energized;
a brush attachment that couples to the handle, the brush attachment comprising:
   a bristle section;
   an electric element located in the brush attachment; and
   a second means that is arranged within or on the brush attachment that receives electromagnetic wave energy emitted by the first means when the brush attachment is coupled to the handle and wherein the second means powers the electric element;
an electric motor arranged within the handle;
a battery that powers the electric motor, the battery being arranged within the handle;
a shaft having a first end operatively connected to the motor and a second end that operatively connects to the brush attachment when the brush attachment is coupled to the handle, wherein the electric motor oscillates the bristle section when the electric motor is energized; and
an electronic control device disposed in the handle that controls the electric motor.

* * * * *